US006013471A

United States Patent [19]
Tindall et al.

[11] Patent Number: 6,013,471
[45] Date of Patent: Jan. 11, 2000

[54] DNA ENCODING HK2 VARIANT POLYPEPTIDES

[75] Inventors: Donald J. Tindall; Charles Y. F. Young, both of Rochester, Minn.; Mohammad Saeed Saedi; Abhay Kumar, both of San Diego, Calif.

[73] Assignees: Hybritech Incorporated, San Diego, Calif.; Mayo Foundation for Medical Education and Research, Rochester, Minn.

[21] Appl. No.: 08/768,859

[22] Filed: Dec. 17, 1996

Related U.S. Application Data

[60] Division of application No. 08/427,767, May 2, 1995, abandoned, which is a continuation-in-part of application No. 08/241,174, May 10, 1994, abandoned.

[51] Int. Cl.[7] .......................... C12P 21/06; C12N 15/00; C07H 21/04; A61K 38/00
[52] U.S. Cl. .................... 435/69.1; 435/320.1; 536/23.5; 530/324; 530/350
[58] Field of Search .................................. 536/23.2, 23.5; 435/69.6, 69.1, 320.1; 530/324, 350

[56] References Cited

U.S. PATENT DOCUMENTS

| | | | |
|---|---|---|---|
| 3,817,837 | 6/1974 | Rubenstein et al. | 195/103 |
| 3,842,067 | 10/1974 | Sarantakis | 260/112 |
| 3,850,752 | 11/1974 | Schuurs et al. | 195/103 |
| 3,862,925 | 1/1975 | Sarantakis et al. | 260/112 |
| 3,901,654 | 8/1975 | Gross | 23/230 |
| 3,935,074 | 1/1976 | Rubenstein et al. | 195/103 |
| 3,972,859 | 8/1976 | Fujino et al. | 260/112 |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,092,408 | 5/1978 | Litt | 424/1 |
| 4,098,876 | 7/1978 | Piasio et al. | 424/1 |
| 4,105,602 | 8/1978 | Colescott et al. | 260/8 |
| 4,353,982 | 10/1982 | Gomez et al. | 435/7 |
| 4,371,515 | 2/1983 | Chu | 436/544 |
| 4,446,122 | 5/1984 | Chu et al. | 424/1 |
| 4,487,715 | 12/1984 | Nitecki et al. | 260/112 |
| 4,629,783 | 12/1986 | Cosand et al. | 530/324 |
| 4,757,048 | 7/1988 | Lewicki et al. | 514/11 |
| 4,792,528 | 12/1988 | Canfield et al. | 436/515 |
| 5,516,639 | 5/1996 | Tindall et al. | 435/7.4 |

FOREIGN PATENT DOCUMENTS

| | | | |
|---|---|---|---|
| 0297913 | 1/1989 | European Pat. Off. | |
| 94/10343 | 5/1994 | WIPO | C12Q 1/68 |
| 94/07329 | 2/1995 | WIPO | |
| 95/03334 | 2/1995 | WIPO | C07K 16/40 |
| 96/26442 | 8/1996 | WIPO | C01N 33/574 |

OTHER PUBLICATIONS

P Altman, et al., "Inbred and Genetically Defined Strains of Laboratory Animals", *Biological Handbooks, III, Federation of American Societies for Experimental Biology,* pp. 21–29, (1992).

P. Andrews, et al., "Tumor–promoting Phorbol Ester Down–Regulates the Androgen Induction of Prostate–specific Antigen in a Human Prostatic Adenocarcinoma Cell Line", *Cancer Research,* 52, 1525–1529, (Mar., 1992).

A. Angermann, et al., "Purifications and characterizations of human salivary–gland prokallikrein from recombinant baculovirus–infected insect cells", *Eur. J. Biochem.,* 206, 225–233, (1992).

A. Baker, et al., "Human Kidney Kallikrein: cDNA Cloning and Sequence Analysis", *DNA,* 4, 445–450, (1985).

T. Berg, et al., "A Common Nomenclature for Members of the Tissue (Glandular) Kallikrein Gene Families", *Recent Progress on Kinins,* Birkhauser Verlag, Basel, 19–25, (1992).

L. Carpino, et al., "The 9–Fluorenylmethoxycarbonyl Amino–Protecting Group", *J. Org. Chem.,* 37, 3404–3409, (1972).

C. Chang, et al., "Solid–phase peptide synthesis using mild base cleavage of Na–fluorenylmethyloxycarbonlyamino acids, exemplified by a synthesis of dihydrosomatostatin", *Int. J. Pept. Pro. Res.,* 11, 246–249, (1978).

P. Chapdelaine, et al., "High Level Expression in the Prostate of a Human Glandular Kallikrein mRNA Related to Prostate–Specific Antigen", *FEBS Lett.,* 236, 205–208, (Aug., 1988).

J. Clements, "The Glandular Kallikrein Family of Enzymes: Tissue–Specific Expression and Hormonal Regulation", *Endocr. Rev.,* 10, 393–419, (1989).

P. Cohen, et al., "Biological Effects of PS as an IGFBP–3 Protease", *In: Program and Abstracts, 74th Annual Meeting of the Endocrine Society,* San Antonio, TX, p. 291, Abstract No. 960, ((Jun. 24–27, 1992)).

M. Digby, et al., "Human prostate specific antigen (PSA) gene: structure and linkage to the kallikrein–like gene", *Nuc. Acids Res.,* 17, 2137, (1989).

B. Evans, et al., "Structure and Chromosomal Localization of the Human Renal kallikrein Gene", *Biochemistry,* 27, 3124–3129, (1988).

D. Fukusima, et al., "Nucleotide Sequence of Cloned cDNA for Human Pancreatic Kallikrein", *Biochemistry,* 24, 8037, (1985).

Pirkko Henttu, et al., "cDNA Coding for the Entire Human prostate Specific Antigen Shows High Homologies to the Human Tissue Kallikrein Genes", *Biochemical and Biophysical Research Communications,* 160, 903–910 (Apr. 28, 1989).

(List continued on next page.)

*Primary Examiner*—Sheela Huff
*Assistant Examiner*—Yvonne Eyler
*Attorney, Agent, or Firm*—Schwegman, Lundberg, Woessner & Kluth, P.A.

[57] ABSTRACT

Isolated nucleic acid molecules encoding variant hK2 polypeptides and fragments thereof, as well as expression cassettes and host cells comprising said nucleic acid molecules, are provided. Also provided is a method to express a nucleic acid molecule encoding a variant hK2 polypeptide.

17 Claims, 12 Drawing Sheets

OTHER PUBLICATIONS

P. Henttu, et al., "Expression of the Gene Coding for Human Prostate–Specific Antigen and Related hGK–1 in Benign and Malignant Tumors of the Human Prostate", *Int. J. Cancer,* 45, 654–660, (1990).

C S Hill, et al., "The preparation of Monoclonal Antibodies Which React Preferentially with Human Bone Alkaline Phosphatase and not Liver Alkaline Phosphatase", *Clinica Chemica Acta,* 186, 315–320, (1989).

C. Killian, et al., "Mitogenic Response of Osteoblast Cells to Prostate–Specific Antigen Suggests an Activation of Latent TGF–6 and a Proteolytic Modulation of Cell Adhesive Receptors", *Biochem. Biophys. Res. Comm.,* 192, 940, (1993).

K. Kuus–reichel, et al., "Production of IgG Monoclonal Antibodes to the Tumor Associated Antigen, CA–195", *Hybridoma,* 13, pp. 31–36 (1994).

U. K. Laemmli, "Cleavage of Structural Proteins during the Assembly of the Head of Bacteriophage T4", *Nature,* 227, 680–685, (Aug., 1970).

M. Lebeau, et al., "Report of the committee on the genetic constitution of chromosomes 18 and 19", *Cytogenet. Cell Genet.,* 51, 338–357, (1989).

F. Lottspeich, et al., "N–Terminal Amino Acid Sequence of Human Urinary Kallikrein Homology with Other Serine Proteases", *Hoppe–Seyler's Z. Physiol. Chem.,* 360, 1947–1950, (Dec., 1979).

H. Lu, et al., "Human Urinary Kallikrein", *Int. J. Peptide Protein Res.,* 33, 237–249, (1989).

V. A. Luckow, et al., "Trends in the Development of Baculovirus Expression Vectors", *Bio/Technology,* 6, pp. 47–55, (Jan. 1988).

A. Lundwall, "Characterization of the gene for Prostate–specific antigen, a human glandular kallikrein", *Biochem. Biophys. Research Comm.,* 161, 1151–1159, (Jun., 1989).

A. Lundwall, et al., "Molecular cloning of human prostate specific antigen cDNA", *FEBS Lett.,* 214, 317–322, (Apr., 1987).

R. McCormack, et al., "Molecular Forms of Prostate–Specific Antigen and the Human Kallikrein Gene Family: A New Era", *Urology,* 45, 729–744, (May 1995).

R. Merrifield, "Solid Phase Peptide Synthesis. I. The Synthesis of a Tetrapeptide", *J. Am. Chem. Soc.,* 85, 2149–2154, (Jul., 1963).

B. Montgomery, et al., "Hormonal Regulation of Prostate–Specific Antigen (PSA) Glycoprotein in the Human Prostatic Adenocarcinoma Cell Line, LNCaP", *The Prostate,* 21, 63–73, (1992).

B. Morris, "hGK–1: A Kallikrein Gene Expressed in Human Prostate", *Clin. Exp. Pharmacol. Physiol,* 16, 345–351, (1989).

P. Murtha, et al., "Androgen Induction of a Human Prostate–Specific Kallikrein hKLK2: Characterization of an Androgen Response Element in he 5' Promoter Region of the Gene", *Biochemistry,* 32, 6459–6464, (1993).

G. Paradis, et al., "Looking for Human Glandular Kallikrein–1 in the Prostate", *The Prostate,* 15, 343–353, (1989).

S. Qui, et al., "In Situ Hybridization of Prostate–Specific Antigen mRNA in Human Prostate", *J. Urology,* 144, 1550–1556, (1990).

J. P. Ransom, "Practical Competitive Binding Assay Methods;", The C. V. Mosby Company, St. Louis, 1–9, 54–61, (1976).

P. Riegman, et al., "Characterization of the Prostate–Specific Antigen Gene: A Novel Human Kallikrein–Like Gene", *Biochem. Biophys. Res. Comm.,* 159, 95–102, (Feb., 1989).

P. Riegman, et al., "Identification and Androgen–Regulated Expression of Two Major Human Glandular Kallikrein–1 (hKG–+) mRNA Species", *Mol. Cell. Endocrinol.,* 76, 181–190, (1991).

P. Riegman, et al., "The prostate–specific antigen gene and the human glandular kallikrein–1 gene are tandemly located on chromosome 19", *FEBS Lett.,* 247, 123–126, (Apr., 1989).

H. Ropers, et al., "Report of the committee on the genetic constitution of chromosome 19", *Cytogenet. Cell Genet.,* 55, 218–228, (1990).

A. Rosenberg, et al., "Vectors for selective expression of cloned DNAs by T7 RNA polymerase", *Gene,* 56, 125–135, (1987).

M. S. Saedi, et al., "Overexpression of a human prostate–specific glandular kallikrein hK2, in *E. coli* and generation of antibodies", *Molecular and Cellular Endocrinology,* 109, 237–241, (Feb., 1995).

L. J. Schedlich, et al., "Kallikrein Genes: Cloning in Man and Expression in Rat Renal Hypertension", *Journal of Hypertension Supplement,* 6, S395–S398, (Dec., 1988).

L. Schedlich, et al., "Primary Structure of a Human Glandular Kallikrein Gene", *DNA,* 6, 429–437, (1987).

L. J. Schedlich, et al., "Three Alu Repeated Sequences Associated with a Human Glandular Kallikrein Gene", *Clin. Exper. Pharmacology & Physiology,* 15, 339–344, (1988).

P. Schulz, et al., "Sequence of a cDNA clone encompassing the complete mature human prostate specific antigen (PSA) and an unspliced leader sequence", *Nuc. Acids Res.,* 16, 6226, (1988).

C. Scorer, et al., "Rapid Selection Using G418 of High Copy Number Transformants of Pichia pastoris for High–Level Foreign Gene Expression", *Biol/Technology,* 12, 181–184, (Feb., 1994).

G. Sutherland, et al., "Human prostate–specific antigen (APS) is a member of the glandular kallikrein gene family at 19p13", *Cytogenet. Cell Genet.,* 48, 205–207, (1988).

P. Tijssen, "Practice and Theory of Enzyme Immunoassays", *In Laboratory Techniques in Biochemistry and Molecular Biology,* vol. 15, R.H. Burdon, (ed.), Elsevier, New York, 43–78, 95–121, 297–3, (1985).

J. Wang, et al., "Purification and Characterization of recombinant tissue kallikrein from *Escherichia coli* and yeast", *Biochem. J.,* 276, 63–61, (1991).

K. Watt, et al., "Human prostate–specific antigen: structural and functional similarity with serine proteases", *PNAS USA,* 83, 3166–3170, (May, 1990).

C. Young, et al., "Abstract of Androgenic Regulation of Kallikrein Gene Expression in Human Prostate Cells", *The Endocrine Society Annual Meeting,* (1990).

C. Young, et al., "Hormonal Regulation of Prostate–Specific Antigen Messenger RNA in Human Prostatic Adenocarcinoma Cell Line LNCap", *Cancer Research,* 51, 3748–3752, (Jul., 1991).

C. Young, et al., "Tissue Specific and Hormonal Regulation of Human Prostate–Specific Glandular Kallikrein", *Biochemistry,* 31, 818–824, (1992).

Ashley, P.L., et al., "Kallikrein–Related mRNAs of the Rat Submaxillary Gland: Nucleotide Sequences of Four Distinct Types Including Tonin", *Biochemistry,* 24, 4512–4520 (1985).

Ashlye, P.L., et al., "Tissue–Specific Expression of Kallikrein–Related Genes in the Rat", *Biochemistry,* 24, 4520–4527 (1985).

Husmann, D.A., et al., "Antipeptide Antibodies to Two Distinct Regions of the Androgen Receptor Localize the Receptor Protein to the Nuclei of Target Cells in the Rat and Human Prostate", *Endocrinology,* 126, 2359–2368 (1990).

van Leeuwen, B.H., et al., "Mouse Glandular Kallikrein Genes", *J. Bio. Chem.,* 261, 5529–5535, (1986).

Deguchi, T., et al., "Detection of Micrometastic Prostate Cancer Cells in Lymph Nodes by Reverse Transcriptase–Polymerase Chain Reaction", *Cancer Research,* 53, 5350–5354 (Nov. 15, 1993).

Takayama, T.K., et al., "Newer Applications of Serum Prostate–Specific Antigen in the Management of Prostate Cancer", *Seminars in Oncology,* 21, 542–553 (Oct. 1994).

Henttu et al. (1989) Biochem. Biophys Res. Comm. 160(2):903–10, 1989.

Riegman et al (1989) Biochem. Biophys. Res. Comm. 159(1):95–102, 1989.

Riegman et al. (1991) Molec. Cell. Endocrinol. 76:181–90, 1991.

Schedlich et al (1987) DNA 6(5):429–37, 1987.

Sambrook et al Molecular Cloning, A Laboratory Manual Cold Spr. Harbor Lab. Press Ch. 12 & 16, 1989.

Bridon, D.P., et al., "Sturctural Comparision of Prostate–Specific Antigen and human glandular kallikrein Using Molecular Modeling", *Urology,* 45, 801–806, (1995).

Christensson, A.C., et al., "Enzymatic Activity of Prostate–Specific Antigen and its Reactions with Extracellular Serine Proteinase Inhibitors", *Eur. J. Biochem.,* 194, 755–763, (1990).

Christensson, A., et al., "Serum Prostate Specific Antigen Complexed to a1–Antichymotrypsin as an Indicator of Prostate Cancer", *J. Urol,* 150, 100–105, (1993).

Clements, J.A., et al., "The Human Kallikrein Gene Family: A Diversity of Expression and Function", *Mol. Cell. Endocrinol.,* 99, c1–6, (1994).

Drinkwater, C.C., et al., "Kallikreins, Kinins and Growth Factor Biosynthesis", *Trends Biochem. Sci.,* 13, 169–172, (1988).

Jones, T.H., et al., "Bioregulatory Role of the Kallikrein–Kinin System in the Normal Pituitary Gland and Its Tumors", *Acta Endocrinol,* 127, 481–484, (1992).

Leinonen, J., et al., "Double–Labeled Time–Resolved Immunoflucrometric Assay of Prostate–Specific Antigen and of its Complex with a1–Antichymotrypsin", *Clin. Chem.,* 39, 2098–2103, (1993).

Okaneya, T., et al., "Overexpression of a Prostate–Specific Glandular Kallikrein hK2 Protein Using a Baculovirus Expression System", *Abtract, Soc. for Basic Urologic Res.,* May 13–14, (1994).

Rahn, H.P., et al., "Expression of Human Salivary–Gland Kallikrein in Insect Cells by a Baculovirus Vector", *In: Recent Progress in Kinins,* H. Fritz, et al., (eds.), Birkhauser Verlag, Basel, 66–73, (1992).

Sambrook, J., et al., "Screening Expression Libraries with Antibodies and Oligonucleotides", *Molecular Cloning, a Laboratory Manual,* 2nd Edition, pp. 12.2–12.15, (1989).

Vinhinen, M., "Modeling of Prostate Specific Antigen and Human Glandular Kallikrein Structures", *Biochem. Biophys. Res. Comm.,* 204, 1251–1256, (1994).

Young, C.F., et al., "Expression and Androgenic Regulation of Human Prostate Specific Kallikreins", *J. Androl,* 16, 97–99, (1995).

```
                    41
hK2:   IVGGWECEKHSQPWQVAVYSHGWAHCGGVLVHPQWVLTAAHCLKKNSQVWLGRHN
hK3:   IVGGWECEKHSQPWQVLVASRGRAVCGGVLVHPQWVLTAAHCIRNKSVILLGRHS

56
LFEPEDTGQRVPVSHSFPHPLYNMSLLKHQSLRPDEDSSHDLMLLRLSEPAKIT
LFHPEDTGQVFQVSTSFPHPLYDMSLLKNRFLRPGDDSSHDLMLLRLSEPAELT 110                                           153
DVVKVLGLPTQEPALGTTCYASGWGSIEPEEFLRPRSLQCVSLHLLSNDMCA
DAVKVMDLPTQEPALGTTCYASGWGSIEPEEFLTPKKLQCVQLHVISNDVCA 162  167
RAYSEKVTEFMLCAGLWTGGKDTCGGDSGGPLVCNGVLQGITSWGPEPCALPEKP
QVHPQKVTKFMLCAGRWTGGKSTCSGDSGGPLVCNGVLQGITSWGSEPCALPERP 217                      237
AVYTKVVHYRKWIKDTIAANP
SLYTKVVHYRKWIKDTIVANP
```

FIG. 4

```
       BamH1 ┐   ┌ pphK2                                              ┌ phK2
          \  │  /                                                    \
   1   GGATCCAGCATGTGGGACCTGGTTCTCTCCATCGCCTTGTCTGTGGGGTGCACTGGTGCCGTGCC
       CCTAGGTCGTACACCCTGGACCAAGAGAGGTAGCGGAACAGACACCCCACGTGACCACGGCACGG
             1▸ MetTrpAspLeuValLeuSerIleAlaLeuSerValGlyCysThrGlyAlaValPr ┌ mhK2
  66   CCTCATCCAGTCTCGGATTGTGGGAGGCTGGGAGTGTGAGAAGCATTCCCAACCCTGGCAGGTGG
       GGAGTAGGTCAGAGCCTAACACCCTCCGACCCTCACACTCTTCGTAAGGGTTGGGACCGTCCACC
  19▸  oLeuIleGlnSerArgIleValGlyGlyTrpGluCysGluLysHisSerGlnProTrpGlnValA 131   CTGTGTACAGTCATGGATGGGCACACTGTGGGGGTGTCCTGGTGCACCCCAGTGGGTGCTCACA
       GACACATGTCAGTACCTACCCGTGTGACACCCCACAGGACCACGTGGGGGTCACCCACGAGTGT
  41▸  laValTyrSerHisGlyTrpAlaHisCysGlyGlyValLeuValHisProGlnTrpValLeuThr 196   GCTGCCCATTGCCTAAAGAAGAATAGCCAGGTCTGGCTGGGTCGGCACAACCTGTTTGAGCCTGA
       CGACGGGTAACGGATTTCTTCTTATCGGTCCAGACCGACCCAGCCGTGTTGGACAAACTCGGACT
  63▸  AlaAlaHisCysLeuLysLysAsnSerGlnValTrpLeuGlyArgHisAsnLeuPheGluProGl 261   AGACACAGGCCAGAGGGTCCCTGTCAGCCACAGCTTCCCACACCCGCTCTACAATATGAGCCTTC
       TCTGTGTCCGGTCTCCCAGGGACAGTCGGTGTCGAAGGGTGTGGGCGAGATGTTATACTCGGAAG
  84▸  uAspThrGlyGlnArgValProValSerHisSerPheProHisProLeuTyrAsnMetSerLeuL 326   TGAAGCATCAAAGCCTTAGACCAGATGAAGACTCCAGCCATGACCTCATGCTGCTCCGCCTGTCA
       ACTTCGTAGTTTCGGAATCTGGTCTACTTCTGAGGTCGGTACTGGAGTACGACGAGGCGGACAGT
 106▸  euLysHisGlnSerLeuArgProAspGluAspSerSerHisAspLeuMetLeuLeuArgLeuSer 391   GAGCCTGCCAAGATCACAGATGTTGTGAAGGTCCTGGGCCTGCCCACCCAGGAGCCAGCACTGGG
       CTCGGACGGTTCTAGTGTCTACAACACTTCCAGGACCCGGACGGGTGGGTCCTCGGTCGTGACCC
 128▸  GluProAlaLysIleThrAspValValLysValLeuGlyLeuProThrGlnGluProAlaLeuGl 456   GACCACCTGCTACGCCTCAGGCTGGGGCAGCATCGAACCAGAGGAGTTCTTGCGCCCCAGGAGTC
       CTGGTGGACGATGCGGAGTCCGACCCCGTCGTAGCTTGGTCTCCTCAAGAACGCGGGGTCCTCAG
 149▸  yThrThrCysTyrAlaSerGlyTrpGlySerIleGluProGluGluPheLeuArgProArgSerL 521   TTCAGTGTGTGAGCCTCCATCTCCTGTCCAATGACATGTGTGCTAGAGCTTACTCTGAGAAGGTG
       AAGTCACACACTCGGAGGTAGAGGACAGGTTACTGTACACACGATCTCGAATGAGACTCTTCCAC
 171▸  euGlnCysValSerLeuHisLeuLeuSerAsnAspMetCysAlaArgAlaTyrSerGluLysVal 586   ACAGAGTTCATGTTGTGTGCTGGGCTCTGGACAGGTGGTAAAGACACTTGTGGGGGTGATTCTGG
       TGTCTCAAGTACAACACACGACCCGAGACCTGTCCACCATTTCTGTGAACACCCCCACTAAGACC
 193▸  ThrGluPheMetLeuCysAlaGlyLeuTrpThrGlyGlyLysAspThrCysGlyGlyAspSerGl 651   GGGTCCACTTGTCTGTAATGGTGTGCTTCAAGGTATCACATCATGGGGCCCTGAGCCATGTGCCC
       CCCAGGTGAACAGACATTACCACACGAAGTTCCATAGTGTAGTACCCCGGGACTCGGTACACGGG
 214▸  yGlyProLeuValCysAsnGlyValLeuGlnGlyIleThrSerTrpGlyProGluProCysAlaL 716   TGCCTGAAAAGCCTGCTGTGTACACCAAGGTGGTGCATTACCGGAAGTGGATCAAGGACACCATC
       ACGGACTTTTCGGACGACACATGTGGTTCCACCACGTAATGGCCTTCACCTAGTTCATGTGGTAG
 236▸  euProGluLysProAlaValTyrThrLysValValHisTyrArgLysTrpIleLysAspThrIle 781   GCAGCCAACCCCTGAGTGCCCCTGTCCCACCCCTACCTCTAGTAAACTGCAG
       CGTCGGTTGGGGACTCACGGGGACAGGGTGGGGATGGAGATCATTTGACGTC         ┐
 258▸  AlaAlaAsnPro                                                 └▸ PstI
```

FIG. 5

```
  1    GAATTCATGATTGTGGGAGGCTGGGAGTGTGAGAAGCATTCCCAACCC
       CTTAAGTACTAACACCCTCCGACCCTCACACTCTTCGTAAGGGTTGGG
  1►      MetIleValGlyGlyTrpGluCysGluLysHisSerGlnPro

49    TGGCAGGTGGCTGTGTACAGTCATGGATGGGCACACTGTGGGGGTGTC
       ACCGTCCACCGACACATGTCAGTACCTACCCGTGTGACACCCCCACAG
 15►   TrpGlnValAlaValTyrSerHisGlyTrpAlaHisCysGlyGlyVal

97    CTGGTGCACCCCCAGTGGGTGCTCACAGCTGCCCATTGCCTAAAGAAG
       GACCACGTGGGGGTCACCCACGAGTGTCGACGGGTAACGGATTTCTTC
 31►   LeuValHisProGlnTrpValLeuThrAlaAlaHisCysLeuLysLys

145    AATAGCCAGGTCTGGCTGGGTCGGCACAACCTGTTTGAGCCTGAAGAC
       TTATCGGTCCAGACCGACCCAGCCGTGTTGGACAAACTCGGACTTCTG
 47►   AsnSerGlnValTrpLeuGlyArgHisAsnLeuPheGluProGluAsp

193    ACAGGCCAGAGGGTCCCTGTCAGCCACAGCTTCCCACACCCGCTCTAC
       TGTCCGGTCTCCCAGGGACAGTCGGTGTCGAAGGGTGTGGGCGAGATG
 63►   ThrGlyGlnArgValProValSerHisSerPheProHisProLeuTyr

241    AATATGAGCCTTCTGAAGCATCAAAGCCTTAGACCAGATGAAGACTCC
       TTATACTCGGAAGACTTCGTAGTTTCGGAATCTGGTCTACTTCTGAGG
 79►   AsnMetSerLeuLeuLysHisGlnSerLeuArgProAspGluAspSer

289    AGCCATGACCTCATGCTGCTCCGCCTGTCAGAGCCTGCCAAGATCACA
       TCGGTACTGGAGTACGACGAGGCGGACAGTCTCGGACGGTTCTAGTGT
 95►   SerHisAspLeuMetLeuLeuArgLeuSerGluProAlaLysIleThr

337    GATGTTGTGAAGGTCCTGGGCCTGCCCACCCAGGAGCCAGCACTGGGG
       CTACAACACTTCCAGGACCCGGACGGGTGGGTCCTCGGTCGTGACCCC
111►   AspValValLysValLeuGlyLeuProThrGlnGluProAlaLeuGly

385    ACCACCTGCTACGCCTCAGGCTGGGGCAGCATCGAACCAGAGGAGTTC
       TGGTGGACGATGCGGAGTCCGACCCCGTCGTAGCTTGGTCTCCTCAAG
127►   ThrThrCysTyrAlaSerGlyTrpGlySerIleGluProGluGluPhe

433    TTGCGCCCCAGGAGTCTTCAGTGTGTGAGCCTCCATCTCCTGTCCAAT
       AACGCGGGGTCCTCAGAAGTCACACACTCGGAGGTAGAGGACAGGTTA
143►   LeuArgProArgSerLeuGlnCysValSerLeuHisLeuLeuSerAsn

481    GACATGTGTGCTAGAGCTTACTCTGAGAAGGTGACAGAGTTCATGTTG
       CTGTACACACGATCTCGAATGAGACTCTTCCACTGTCTCAAGTACAAC
159►   AspMetCysAlaArgAlaTyrSerGluLysValThrGluPheMetLeu

529    TGTGCTGGGCTCTGGACAGGTGGTAAAGACACTTGTGGGGGTGATTCT
       ACACGACCCGAGACCTGTCCACCATTTCTGTGAACACCCCCACTAAGA
175►   CysAlaGlyLeuTrpThrGlyGlyLysAspThrCysGlyGlyAspSer

577    GGGGGTCCACTTGTCTGTAATGGTGTGCTTCAAGGTATCACATCATGG
       CCCCCAGGTGAACAGACATTACCACACGAAGTTCCATAGTGTAGTACC
191►   GlyGlyProLeuValCysAsnGlyValLeuGlnGlyIleThrSerTrp

625    GGCCCTGAGCCATGTGCCCTGCCTGAAAAGCCTGCTGTGTACACCAAG
       CCGGGACTCGGTACACGGGACGGACTTTTCGGACGACACATGTGGTTC
207►   GlyProGluProCysAlaLeuProGluLysProAlaValTyrThrLys

673    GTGGTGCATTACCGGAAGTGGATCAAGGACACCATCGCAGCCAACCCC
       CACCACGTAATGGCCTTCACCTAGTTCATGTGGTAGCGTCGGTTGGGG
223►   ValValHisTyrArgLysTrpIleLysAspThrIleAlaAlaAsnPro

721    TGAGTGCCCCTGTCCCACCCCTACCTCTAGTAAACTGCAG
       ACTCACGGGGACAGGGTGGGGATGGAGATCATTTGACGTC
```

FIG. 6

```
  1   GTGCCCCTCATCCAGTCTCGGATTGTGGGAGGCTGGGAGTGTGAGAAGCATTCCCAACCC
      CACGGGGAGTAGGTCAGAGCCTAACACCCTCCGACCCTCACACTCTTCGTAAGGGTTGGG
  1►  ValProLeuIleGlnSerArgIleValGlyGlyTrpGluCysGluLysHisSerGlnPro

61   TGGCAGGTGGCTGTGTACAGTCATGGATGGGCACACTGTGGGGGTGTCCTGGTGCACCCC
      ACCGTCCACCGACACATGTCAGTACCTACCCGTGTGACACCCCCACAGGACCACGTGGGG
 21►  TrpGlnValAlaValTyrSerHisGlyTrpAlaHisCysGlyGlyValLeuValHisPro

121   CAGTGGGTGCTCACAGCTGCCCATTGCCTAAAGAAGAATAGCCAGGTCTGGCTGGGTCGG
      GTCACCCACGAGTGTCGACGGGTAACGGATTTCTTCTTATCGGTCCAGACCGACCCAGCC
 41►  GlnTrpValLeuThrAlaAlaHisCysLeuLysLysAsnSerGlnValTrpLeuGlyArg

181   CACAACCTGTTTGAGCCTGAAGACACAGGCCAGAGGGTCCCTGTCAGCCACAGCTTCCCA
      GTGTTGGACAAACTCGGACTTCTGTGTCCGGTCTCCCAGGGACAGTCGGTGTCGAAGGGT
 61►  HisAsnLeuPheGluProGluAspThrGlyGlnArgValProValSerHisSerPhePro

241   CACCCGCTCTACAATATGAGCCTTCTGAAGCATCAAAGCCTTAGACCAGATGAAGACTCC
      GTGGGCGAGATGTTATACTCGGAAGACTTCGTAGTTTCGGAATCTGGTCTACTTCTGAGG
 81►  HisProLeuTyrAsnMetSerLeuLeuLysHisGlnSerLeuArgProAspGluAspSer

301   AGCCATGACCTCATGCTGCTCCGCCTGTCAGAGCCTGCCAAGATCACAGATGTTGTGAAG
      TCGGTACTGGAGTACGACGAGGCGGACAGTCTCGGACGGTTCTAGTGTCTACAACACTTC
101►  SerHisAspLeuMetLeuLeuArgLeuSerGluProAlaLysIleThrAspValValLys

361   GTCCTGGGCCTGCCCACCCAGGAGCCAGCACTGGGGACCACCTGCTACGCCTCAGGCTGG
      CAGGACCCGGACGGGTGGGTCCTCGGTCGTGACCCCTGGTGGACGATGCGGAGTCCGACC
121►  ValLeuGlyLeuProThrGlnGluProAlaLeuGlyThrThrCysTyrAlaSerGlyTrp

421   GGCAGCATCGAACCAGAGGAGTTCTTGCGCCCCAGGAGTCTTCAGTGTGTGAGCCTCCAT
      CCGTCGTAGCTTGGTCTCCTCAAGAACGCGGGGTCCTCAGAAGTCACACACTCGGAGGTA
141►  GlySerIleGluProGluGluPheLeuArgProArgSerLeuGlnCysValSerLeuHis

481   CTCCTGTCCAATGACATGTGTGCTAGAGCTTACTCTGAGAAGGTGACAGAGTTCATGTTG
      GAGGACAGGTTACTGTACACACGATCTCGAATGAGACTCTTCCACTGTCTCAAGTACAAC
161►  LeuLeuSerAsnAspMetCysAlaArgAlaTyrSerGluLysValThrGluPheMetLeu

541   TGTGCTGGGCTCTGGACAGGTGGTAAAGACACTTGTGGGGGTGATTCTGGGGGTCCACTT
      ACACGACCCGAGACCTGTCCACCATTTCTGTGAACACCCCCACTAAGACCCCCAGGTGAA
181►  CysAlaGlyLeuTrpThrGlyGlyLysAspThrCysGlyGlyAspSerGlyGlyProLeu

601   GTCTGTAATGGTGTGCTTCAAGGTATCACATCATGGGGCCCTGAGCCATGTGCCCTGCCT
      CAGACATTACCACACGAAGTTCCATAGTGTAGTACCCCGGGACTCGGTACACGGGACGGA
201►  ValCysAsnGlyValLeuGlnGlyIleThrSerTrpGlyProGluProCysAlaLeuPro

661   GAAAAGCCTGCTGTGTACACCAAGGTGGTGCATTACCGGAAGTGGATCAAGGACACCATC
      CTTTTCGGACGACACATGTGGTTCCACCACGTAATGGCCTTCACCTAGTTCATGTGGTAG
221►  GluLysProAlaValTyrThrLysValValHisTyrArgLysTrpIleLysAspThrIle

721   GCAGCCAACCCCTGAGTGCCCCTGTCCCACCCCTACCTCTAGTAAA
      CGTCGGTTGGGGACTCACGGGGACAGGGTGGGGATGGAGATCATTT
241►  AlaAlaAsnPro
```

FIG. 7

DNA ENCODING HK2 VARIANT POLYPEPTIDES

CROSS-REFERENCE TO RELATED APPLICATION

This application is a division of U.S. patent application Ser. No. 08/427,767, filed May 2, 1995, now abandoned which, in turn, is a Continuation-in-Part of U.S. patent application Ser. No. 08/241,174, filed May 10, 1994, now abandoned, the disclosure of which is incorporated by reference herein.

BACKGROUND OF THE INVENTION

The glandular kallikreins are a subgroup of serine proteases which are involved in the post-translational processing of specific polypeptide precursors to their biologically active forms. The human kallikrein gene family consists of three members: prostate-specific antigen, human glandular kallikrein, and pancreatic/renal kallikrein. See J. A. Clements, *Endocr. Rev.*, 10,393 (1989) and T. M. Chu et al. (U.S. Pat. No. 4,446,122). A common nomenclature for these members of the tissue (glandular) kallikrein gene families was recently adopted by T. Berg et al., in *Recent Progress on Kinins: Biochemistry and Molecular Biology of the Kallikrein-Kinin System. Agents and Actions Supplements, Vol. I*, H. Fritz et al., eds., Birkkauser Verlag, Basel (1992), and is defined in Table I, below.

TABLE 1

The Human Tissue Kallikrein Gene Family
(approved species designation: HSA)

| New Designation | Previous Designations | mRNA/cDNA | Protein | New Protein Designation |
|---|---|---|---|---|
| hKLK1 | KLK1 hRKALL | λHK1 and phKK25 cDNAs | tissue kallikrein (renal/pancrease/salivary) | hK1 |
| hKLK2 | KLK2 hGK-1 hKK-3 | | prostate-specific glandular kallikrein | hK2 |
| hKLK2 | PSA PA APS | λHPSA-1 and PSA cDNAs | PSA (prostate-specific antigen) | hK3 |

The DNA sequence homology between hKLK2 and hKLK3 (exon regions) is 80%, whereas the homology between hKLK2 and hKLK1 is 65%. The deduced amino acid sequence homology of hK2 to hK1 is 57%. Amino acid sequences deduced by L. J. Schedlich et al., *DNA*, 6, 429 (1987) and B. J. Morris, *Clin. Exp. Pharmacol. Physiol.* 16, 345 (1989) indicate that hK2 may be a trypsin-like serine protease, whereas hK3 (PSA) is a chymotrypsin-like serine protease. Therefore, if hK2 is indeed secretory, it may have a different physiological function than hK3.

The hKLK2 gene is located about 12 kbp downstream from the hKLK3 gene in a head-to-tail fashion on chromosome 19. (P. H. Riegman et al., *FEBS Lett.*, 247, 123, (1989)). The similarities of gene structure and deduced amino acid sequences of these human kallikreins suggest that their evolution may involve the same ancestral gene. Most interestingly, as reported by Morris, cited supra; P. Chapdelaine, *FEBS Lett.*, 236, 205 (1988); and Young, *Biochemistry*, 31, 1952 (1992), both hK2 and hK3 may be expressed only in the human prostate, while expression of hK1 is limited to the pancreas, submandibular gland, kidney, and other nonprostate tissues.

Tremendous interest has been generated in hK3 (PSA) because of the important role it plays as a marker to detect and to monitor progression of prostate carcinoma. Its usefulness as a marker is based on the elevated serum concentration of circulating hK3 proteins which are frequently associated with prostatic cancer. The serum concentration of hK3 has been found to be proportional to the cancer mass in untreated patients, but is also proportional to the volume of hyperplastic tissue in patients with benign prostatic hyperplasia (BPH). The serum levels of hK3 become reduced following prostate cancer therapy.

Despite the information which can be ascertained about hK2 from the genomic DNA sequence, very little is known about the hK2 polypeptide itself. The reason for this is that the protein has not been purified and characterized. Thus, a need exists for a method to obtain hK2 polypeptide and related polypeptides in sufficient quantity and purity for characterization and for use as therapeutic/diagnostic agents or reagents.

SUMMARY OF THE INVENTION

The present invention provides an isolated, substantially homogenous hK2 polypeptide. As used herein, in the term "hK2 polypeptide" includes pre-pro hK2, pro hK2 and mature hK2 polypeptides. Pre-pro hK2 is secreted by the cell in vivo, and is cleaved during secretion to yield pro hK2, which is then enzymatically cleaved in the extracellular environment to yield "mature" hK2. Most preferably, the hK2 polypeptide is contiguous in amino acid sequence with SEQ ID NO: 16, SEQ ID NO: 6, SEQ ID NO: 19, or SEQ ID NO: 10

The present invention also provides isolated nucleic acid molecules encoding hK2 polypeptide, including (a) a cDNA molecule comprising the nucleotide sequence of the coding region of the hK2 gene; (b) a DNA molecule capable of hybridizing under stringent conditions to a nucleotide sequence complementary to the nucleotide sequence of (a); and (c) a genetic variant of any of the DNA molecules of (a) and (b) which encodes a polypeptide possessing an antigenic function of naturally occurring hK2 polypeptide. Preferably, the nucleic acid comprises a discrete, isolated DNA or RNA molecule encoding the complete hK2 polypeptide, which can include the pre-pro, pro or mature forms. Most preferably, the nucleic acid is a DNA sequence contiguous with SEQ ID NO:5, SEQ ID NO: 7 or SEQ ID NO: 20 e.g., see FIGS. 5, 6 or 7. These DNA sequences can be produced using the polymerase chain reaction (PCR), and novel oligonucleotide primers employed in the synthesis are also an embodiment of the invention.

The nucleic acid sequence also can comprise a promoter operably linked to the nucleic acid sequence. Therefore, the invention also comprises a chimeric expression vector comprising the above-described nucleic acid sequence, operationally linked to control sequences recognized by a host cell transformed with the vector, as well as said transformed host cell, and methods of its preparation and use to produce recombinant hK2. Thus, the present invention also provides a method of using a nucleic acid molecule, such as a cDNA clone encoding hK2 polypeptide, comprising expressing the nucleic acid molecule in a cultured host cell transformed, preferably stably transformed, with a chimeric expression vector comprising said nucleic acid molecule operably linked to control sequences recognized by the host cell transformed with the vector; and recovering the hK2 polypeptide from the transgenic host cell, i.e., from the culture medium. As used herein, the term "chimeric" means that the vector comprises DNA from at least two different species, or comprises DNA from the same species, which is linked or associated in a manner which does not occur in the "native" form of said species.

More specifically, E. coli and baculovirus insect cells systems have been employed to produce hK2 polypeptides in two forms, i.e. pre-pro hK2 (pphK2) and mature hK2 (mhK2). Thus, the present invention provides the first example of the overexpression of hK2 in heterologous systems. However, although pphK2 produced in E. coli has proven to be an invaluable resource for generating antibodies to the denatured form of the protein, it is desirable to both discern the steps involved in the biosynthesis of hK2 and to obtain antibodies specific for the fully processed and secreted form of the protein. Therefore, mammalian cell systems have been employed to produce hK2 polypeptides. Thus, the present invention also provides the first example of the expression of hK2 in mammalian cells and purification and characterization of the secreted protein.

The high degree of amino acid sequence homology of hK2 with hK3 indicates that measuring serum concentrations of both proteins may be useful in the diagnosis and monitoring of prostate cancer. For example, the antibodies developed against hK3 now used in these assays could theoretically also recognize hK2, because of mutual contamination in the antigenic preparations used to develop the anti-hK3 antibodies or because of antibody cross-reactivity between these two proteins. This could account for the substantial percentage of false positive results which are observed in current hK3 assays. On the other hand, if circulating hK2 levels are also elevated above baseline levels in prostate cancer patients, detection of hK2 by hK2-specific antibodies could provide an alternative, confirmatory assay for prostate cancer.

Therefore, hK2 polypeptide, as well as variants and subunits thereof, produced by the present method can be used to produce populations of antibodies that, in turn, can be used as the basis for assays to detect and quantify hK2 polypeptide (or "protein") in samples derived from tissues such as prostate carcinomas, cells such as prostate cell lines, or from fluids such as seminal fluid or blood. Thus, the present invention also provides populations of monoclonal or polyclonal antibodies that specifically bind to hK2 polypeptide, while not significantly binding to hK3. The term "significantly" is defined by reference to the comparative assays discussed below. These antibodies can also be used in affinity chromatography, to purify mammalian hK2 from natural sources. The isolated, substantially homogeneous hK2 can also be employed as a component in diagnostic assays for "native" hK2 in samples derived from human tissues or physiological fluids. For example, the recombinant hK2 can be bound to a detectable label and employed in competitive immunoassays for hK2, as described in U.S. patent application Ser. No. 08/096,946, filed Jul. 22, 1993, now U.S. Pat. No. 5,516,639 the disclosure of which is specifically incorporated by reference herein.

As used herein with respect to the present invention, the terms "hK2 polypeptide," "hK2 protein," and "hK2" are considered to refer to identical human materials, unless otherwise indicated.

BRIEF DESCRIPTION OF THE FIGURES

FIG. 4 depicts the amino acid sequences of mature hK2 (deduced from cDNA sequence, SEQ ID NO: 16) and hK3 (SEQ ID NO: 1). Underlined sequences denote nonhomologous regions that can be used for preparation of antibodies specific to hK2.

FIG. 5 depicts pphK2 cDNA containing a BamHl site at the 5'end and a Pst1 site at the 3'end (SEQ ID NO: 5) (coding strand is numbered) as well as the amino acid sequence of pre-pro hK2 encoded thereby (SEQ ID NO: 6). The amino acid sequences of pro hK2 and mature hK2 are also shown on the Figure.

FIG. 6 depicts mhK2 cDNA containing an EcoR1 site at the 5'end and Pst1 site at the 3'end (SEQ ID NO: 7), as well as the corresponding amino acid sequence (SEQ ID NO: 8) which encompasses the amino acid sequence of mhK2 polypeptide.

FIG. 7 depicts pro hK2 DNA (SEQ ID NO: 9) (coding strand is numbered) and the amino acid sequence of pro hK2 (SEQ ID NO: 10).

DETAILED DESCRIPTION OF THE INVENTION

Figure 1:
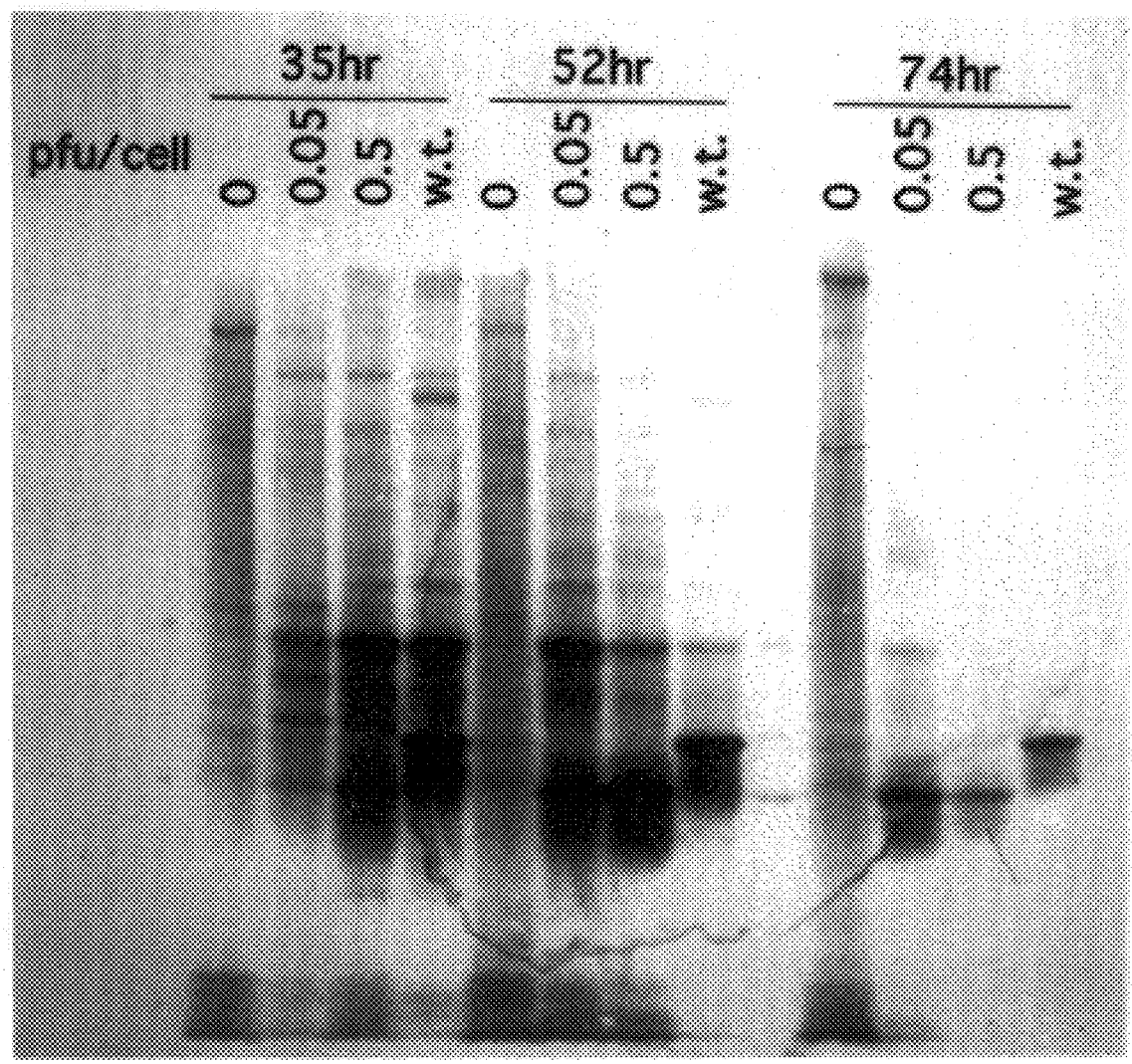
FIG. 1 depicts a time course study of recombinant pphK2 in s.f9 cells infected with recombinant pphK2 virus. At each of the time points cells were depleted of methionine and cysteine for 1 hour in deficient media and then supplemented with [$^{35}$S]-methione and [$^{35}$S]-cysteine. Protein was determined by Bradford assay. Aliquots of protein (20 $\mu$g) were loaded onto a 12% Tris-Glycine SDS gel. A Phosphorimager cassette was exposed overnight. The band of interest is indicated with an arrow. w.t.: wild type.

As used herein, the term "hK2 polypeptide" preferably encompasses the recombinant pre-pro, pro and mature hK2 polypeptides. As proposed herein, a mature hK2 polypeptide having the amino acid sequence shown in FIG. 4 (SEQ ID NO: 16), as well as "variant" polypeptides which share at least 90% homology with SEQ ID NO: 16 in the regions which are substantially homologous with hK3, i.e., which regions are not identified by bars as shown in FIG. 4. Such hK2 polypeptides also possess antigenic function in common with the mature hK2 molecule of FIG. 4, in that said polypeptides are also definable by antibodies which bind specifically thereto, but which do not cross-react with hK3 (or hK1). Preferably, said antibodies react with antigenic sites or epitopes that are also present on the mature hK2 molecule of FIG. 4. Antibodies useful to define common antigenic function are described in detail in Ser. No. 08/096,946, now U.S. Pat. No. 5,516,639. i.e., polyclonal antisera prepared in vivo against hK2 submit 41–56.

"Isolated hK2 nucleic acid" is RNA or DNA containing greater than 15, preferably 20 or more, sequential nucleotide bases that encode a biologically active hK2 polypeptide or a variant fragment thereof, that is complementary to the non-coding strand of the native hK2 polypeptide RNA or DNA, or hybridizes to said RNA or DNA and remains stably bound under stringent conditions. Thus, the RNA or DNA is isolated in that it is free from at least one contaminating nucleic acid with which it is normally associated in the natural source and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated hK2 nucleic acid is RNA or DNA that encodes a biologically active hK2 polypeptide sharing at least 90% sequence identity with the hK3-homologous regions of the hK2 peptide of FIG. 4, as described above. The term "isolated, substantially homogenous" as used with respect to an hK2 polypeptide is defined in terms of the methodologies discussed herein below.

As used herein, the term "recombinant nucleic acid," i.e., "recombinant DNA" refers to a nucleic acid, i.e., to DNA that has been derived or isolated from any appropriate tissue source, that may be subsequently chemically altered in vitro, an later introduced into target host cells, such as cells derived from animal, plant, insect, yeast, fungal or bacterial sources. An example of recombinant DNA "derived" from a source, would be a DNA sequence that is identified as a useful fragment encoding hK2, or a fragment or variant thereof, and which is then chemically synthesized in essentially pure form. An example of such DNA "isolated" from a source would be a useful DNA sequence that is excised or removed from said source by chemical means, e.g, by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome of the host target cell which is the recipient of the DNA, or it is resident in the genome but is not expressed.

The recombinant DNA sequence, used for transformation herein, may be circular or linear, double-stranded or single-stranded. Generally, the DNA sequence is in the form of chimeric DNA, such as plasmid DNA, that can also contain coding regions flanked by control sequences which promote the expression of the recombinant DNA present in the resultant cell line. For example, the recombinant DNA may itself comprise a promoter that is active in mammalian cells, or may utilize a promoter already present in the genome that is the transformation target. Such promoters include the CMV promoter, as well as the SV 40 late promoter and retroviral LTRs (long terminal repeat elements). Aside from recombinant DNA sequences that serve as transcription units for hK2 or portions thereof, a portion of the recombinant DNA may be untranscribed, serving a regulatory or a structural function.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

Aside from recombinant DNA sequences that serve as transcription units for hK2 or portions thereof, a portion of the recombinant DNA may be untranscribed, serving a regulatory or a structural function.

The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt dhfr, bar, aroA, dapA and the like.

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

The recombinant DNA can be readily introduced into the target cells by transfection with an expression vector comprising cDNA encoding hK2, for example, by the modified calcium phosphate precipitation procedure of C. Chen et al., *Mol. Cell. Biol.,*7, 2745 (1987). Transfection can also be accomplished by lipofectin, using commercially available kits, e.g., provided by BRL.

Suitable host cells for the expression of hK2 polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6; 47 (1988); Miller et al., in *Genetic Engineering*, J. K. Setlow et al., eds., Vol. 8 (Plenum Publishing, 1986), pp. 277–279; and Maeda et al., *Nature,* 315:592 (1985). A variety of viral strains for transfection are publicly available, e.g., the L-1 variant of *Autographa californica* NPV and the Bm-5 strain of *Bombyx mori* NPV, and such viruses may be used, preferably for transfection of *Spodoptera frugiperda* cells.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. For example, see Lawn et al., *Nucleic Acids Res.,* 9, 6103–6114 (1981), and Goeddel et al., *Nucleic Acids Res.,* 8, 4057 (1980).

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as 32-P, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Polymerase chain reaction" or "PCR" refers to a procedure or technique in which amounts of a preselected piece of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol,* 51, 263 (1987); Erlich, ed., *PCR Technology,* (Stockton Press, N.Y., 1989).

"Stringent conditions" are those that (1) employ low ionic strength and high temperature for washing, for example, 0.015 M NaC1/0.0015 M sodium citrate (SSC); 0.1% sodium lauryl sulfate (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaC1,75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

When hK2 polypeptide is expressed in a recombinant cell other than one of human origin, the hK2 polypeptide is completely free of proteins or polypeptides of human origin. However, it is necessary to purify hK2 polypeptide from recombinant cell proteins or polypeptides to obtain preparations that are substantially homogeneous as to hK2 polypeptide. For example, the culture medium or lysate can be centrifuged to remove particulate cell debris. The membrane and soluble protein fractions are then separated. The hK2 polypeptide may then be purified from the soluble protein fraction and, if necessary, from the membrane fraction of the culture lysate. HK2 polypeptide can then be purified from contaminant soluble proteins and polypeptides by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; or ligand affinity chromatography.

Once isolated from the resulting transgenic host cells, derivatives and variants of the hK2 polypeptide can be readily prepared. For example, amides of the hK2 polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the hK2 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N-and O-acylation may be carried out together, if desired. In addition, the internal hK2 amino acid sequence of FIG. 4 can be modified by substituting one or two conservative amino acid substitutions for the positions specified, including substitutions which utilize the D rather than L form. The invention is also directed to variant or modified forms of the hK2 polypeptide of FIG. 4. One or more of the residues of this polypeptide can be altered, so long as antigenic function is retained. Conservative amino acid substitutions are preferred—that is, for example, aspartic-glutarnic as acidic amino acids; lysine/arginine/histidine as basic amino acids; leucine/isoleucine, methionine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

Once isolated, hK2 polypeptide and its antigenically active variants, derivatives and fragments thereof can be used in assays for hK2 in samples derived from biological materials suspected of containing hK2 or anti-hK2 antibodies, as disclosed in detail in Ser. No. 08/096,946 now U.S. Pat. No. 5,516,639. For example, the hK2 polypeptide can be labelled with a detectable label, such as via one or more radiolabelled peptidyl residues, and can be used to compete with endogenous hK2 for binding to anti-hK2 antibodies, i.e., as a "capture antigen" to bind to anti-hK2 antibodies in a sample of a physiological fluid, via various competitive immunoassay format for hK2 which uses immobilized anti-hK2 antibodies is carried out by:

(a) providing an amount of anti-hK2 antibodies attached to a solid surface;

(b) mixing the sample of physiological fluid to be tested with a known amount of hK2 polypeptide which comprises a detectable label, to produce a mixed sample;

(c) contacting said antibodies on said solid surface with said mixed sample for a sufficient time to allow immunological reactions to occur between said antibodies and said hK2, and between said antibodies and said labelled polypeptide;

(d) separating the solid surface from the mixed sample;

(e) detecting or determining the presence or amount of labelled polypeptide either bound to the antibodies on the solid surface or remaining in the mixed sample; and (f) determining from the result in step (e) the presence or amount of said hK2 in said sample.

In another format which can detect endogenous hK2 in a sample by a competitive inhibition immunoassay, a known amount of anti-hK2 antibody is added to a sample containing an unknown amount of endogenous hK2. The known amount is selected to be less than the amount required to complex all of the hK2 suspected to be present, e.g., that would be present in a sample of the same amount of physiological fluid obtained from a patient known to be prostate cancer. Next, a known amount of the hK2 polypeptide of the invention or a subunit thereof, comprising a detectable label is added. If endogenous hK2 is present in the sample, fewer antibodies will be available to bind the labelled hK2 polypeptide, and it will remain free in solution. If no endogenous hK2 is present, the added labelled polypeptide will complex with the added anti-hK2 antibodies to form binary complexes. Next, the binary antibody-antigen complexes are precipitated by an anti-mammal IgG antibody (sheep, goat, mouse, etc.). The amount of radioactivity or other label in the precipitate (a ternary complex) is inversely proportional to the amount of endogenous hK2 that is present in the sample, e.g., a pellet containing reduced amounts of radioactivity is indicative of the presence of endogenous hK2.

Alternatively to the conventional techniques for preparing polyclonal antibodies or antisera in laboratory and farm animals, monoclonal antibodies against hK2 polypeptide can be prepared using known hybridoma cell culture techniques. In general, this method involves prepared an antibody- producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the f(ab) fragment, as are partially humanized monoclonal antibodies.

The invention will be further described by reference to the following detailed examples.

EXAMPLE 1

Construction of hK2 Expression Vectors
(A) Generation of Recombinant Baculoviruses Containing pphK2 and mhK2 Coding Sequences A cDNA (approximately 820 bp long) encoding the entire prepro-hK2 (pphK2) (from nucleotide #40 to #858 relative to the start site of the pphK2 transcript), as shown in FIG. 5, was synthesized from RNA of human BPH tissue using reverse-transcription polymerase chain reaction (RT-PCR) technology with a pair of hK2 specific oligonucleotide primers (5' ACGCGGATCCAGCATGTGGGACCTGGT-TCTCT3' SEQ ID NO: 2 and 5' ACAGCTGCAGTTTAC-TAGAGGTAGGGGTGGGAC 3' SEQ ID NO: 3). This cDNA was generated such that 5' and 3' ends (with respect to pphK2 sense sequence) were bracketed with BamH1 and Pst 1 sequences respectively. The cDNA was then purified by agarose gel electrophoresis, and digested with BamH1 and Pst 1 restriction enzymes. The restricted cDNA was ligated with the BamH1-Pst1 digested pVL1393 plasmid vector and transformed into the E.coli HB101 strain. E.coli harboring pphK2 cDNA/pVL1393 plasmid vector were selected and verified by restriction enzyme mapping and DNA sequencing. Plasmid pphK2 cDNA/pVL1393 was mass-produced in E.coli and purified by CsCl gradient ultra-centrifugation.

cDNA encoding the mature hK2 was synthesized using PCR with the aforementioned pphK2 cDNA as the template plus a pair of hK2 oligonucleotides (5' ACGCGGATCCAG-CATGTGGGACCTGGTTCTCT3' SEQ ID NO: 2 and 5' ACCGGAATTCATGATTGTGGGAGGCTGGGAGTGT3' SEQ ID NO: 4). As noted, the 3' end oligonucleotide was the same 3' end oligonucleotide used for synthesizing the pphK2 cDNA. However, the 5' end oligonucleotide was different from the 5' oligonucleotide used for the pphK2 cDNA, and therefore generates a CDNA coding for the mature form of hK2 (mhK2), as shown in FIG. 6. The mhK2 cDNA was bracketed with EcoR1 and Pst1 sequences at the 5' and 3' ends respectively. The protein produced from the mhK2 cDNA will gain an exogenous methionine at its N-terminus. The mhK2/pVL1393 vector was generated and purified as described for pphK2/pVL1393. The DNA sequence analysis for pphK2 and nhK2 in pVL1393 showed that one nucleotide (#805) has been altered (G to T) in a silent mutation.

pphK2/pVL1393 or mhK2/pVL1393 DNA (2 µg) were cotransfected with a linearized Baculogold DNA (0.5 µg; Pharmingen, San Diego, Calif.) into Sf9 insect cells according to Pharmingen instructions (S. Gruenwold et al., baculovirus expression vector system: Procedures and Methods Manual, Pharmingen, San Diego, Calif. (1993)). Four to six days after the transfection, Sf9 cell spent medium containing viral particles was harvested and used to infect fresh Sf9 cells to amplify viral titers. Total RNA was isolated for Northern blot analysis of authentic pphK2 or mhK2 transcript using hK2 cDNA as a probe. Further proof of pphK2 or mhK2 transcript expressed in recombinant virus infected Sf9 cells was obtained by RT-PCR and DNA sequencing. Pure recombinant baculovirus containing pphK2 or mhK2 were obtained by secondary or tertiary plaque purification protocol according to instructions from Pharmingen (S. Gruenwold et al., cited above).

EXAMPLE 2

Generation of Prokaryotic Expression Vector

A 0.8 kb fragment representing the entire preprohK2 (pphK2) coding sequence was generated by polymerase chain reaction (PCR) using primers A (5' TATACATAT-GTGGGACCTGGTTCTCTCC3' SEQ ID NO.: 11) and B (5' ATATGGATCCTCAGGGGTTGGCTGCGATGGT3' SEQ ID NO: 12) and plasmid pVL1393 containing pphK2 as the template. The pphK2 bacterial expression vector (pBPPHK2) was prepared by standard DNA cloning technology, (Sambrook, cited above), to subclone this 0.8 kb fragment into the Nde1/BamH1 site of the plasmid pPHS579 (a gift from Dr. H. Hsiung, Eli Lilly Co, Inc.) under the control of T7 promoter. The DNA of the entire insert plus the cloning sites was sequenced to confirm that no cloning artifacts had occurred and to ensure that no anomalies in the sequence had been generated by PCR. pBPPHK2 was transformed into E.coli BL21 (DE3)Lys S (Novagen, Inc., Madison, Wis.).

EXAMPLE 3

Generation of a Mammalian Expression Vector

To express hK2 in mammalian cell lines, a 0.8 kb fragment representing the entire preprohk2 (pphK2) coding sequence was generated by PCR using primers A(5' ATATG-GATCCATATGTCAGCATGTGGGACCTGGTTC TCTCCA3') SEQ ID NO: 17) and B(5' ATATGGATCCTCAGGGGTTGGCTGCGATGGT3') SEQ ID NO: 12 and plasrnid pVL1393 containing pphK2 as the template. The mammalian expression vector (pGThK2) was prepared using standard DNA cloning technology (Sambrook, 1989), to clone this 0.8 kb fragment into the Bc 1site of the plasmid pGT-d (a gift from Dr. Brian Grinnell, Eli Lilly, Inc.) under control of the GBMT promotor. The DNA of the entire insert plus the cloning sites was sequenced and a single base change at position 650 (T for C) was noted. This change results in an amino acid substitution of valine for alanine at position 217 in hK2. AV12–664 (ATCC CRL-9595), a cell line derived from a adenovirus-induced tumors in Syrian hamster, was grown in Dulbecco's modified Eagle's medium supplemented within 10% fetal bovine serum (D10F) and transfected with plasinid pGThK2 using the calcium phosphate method.

EXAMPLE 4

Identification of Recombinant pphK2 and mhK2
A. Baculovirus—Insect Cell System

Sf9 cells ($7 \times 10^6$/plate) were seeded onto 100 mm Corning plates with 10% fetal calf serum—Graces medium at room temperature for 1 hr. After attachment on culture plates, cells were infected with wild type or recombinant baculovirus in serum free Excell-400 medium and incubated at 27° C. Control cells were grown in the absence of virus. At designated times (24–96 hr) cells were placed in fresh Sf9-IIOO media deficient of either methionine or methionine and cysteine for 45–60 min at 27° C., then incubated with Promix (0.143 mCi/plate; a mixture of [$^{35}$S]-methionine and [$^{35}$S]-cysteine; 1,000–1,400 Ci/mmol; Amersham) in serum free and methionine/cysteine deficient Sf9IIOO medium (Biofluids) for 5–8 hr or 20 hr. After the end of each incubation time, cells and spent media were separated by centrifugation (1,000 rpm; Beckman J-6B; Beckman, Fullerton, Calif.). Cells were washed and centrifuged (13,000 rpm; Biofuge 13, Baxter) twice. The washed cells were lysed by freeze/thaw in a detergent buffer (10 mM Tris, pH 7.5; 130 mM NaCl, 1% Triton X-100, 10 mM NaF; 10 mM NaPi, 10 mM Nappi, pH7.5) or H$_2$O and centrifuged to obtain cytosol and insoluble cellular fractions. Protein contents of the above samples were determined by either the Bradford or Lowry method (BioRad, Inc., Melville, N.Y.). The above spent media, cystosol and insoluble cellular fraction were frozen and stored separately until used. A duplicate set of samples were prepared without $^{35}$S-labeling.

For SDS-polyacrylamide gel electrophoresis (PAGE) analysis of expression of hK2 protein in Sf9 cells, samples were added to sample buffer (U. K. Laemmli, Nature, 227, 680 (1970)), heated at 95° C. for 5 minutes and subjected to SDS-PAGE under reducing conditions.

Northern blot analysis was routinely used to screen and isolate clonal recombinant baculoviruses expressing pphK2 or mhK2 nRNA. A comparison of the corresponding lanes in both autoradiographs of the Northern blot and photographs of ethidium bromide staining of RNA shows that mRNA for pphK2 or mhK2 was present in recombinant virus infected Sf9 but not in wild type virus-infected cells. Moreover, each of the pphK2 or mhK2 mRNA positive lanes represents RNA isolated from Sf9 cells infected with recombinant viruses derived from a single viral plaque. Thus, the results suggest that high frequency (100%) of recombinant baculovirus containing either pphK2 or mhK2 was obtained from the above cotransfection. Furthermore, the sequences of pphK2 or mhK2 expressed in viral infected Sf9 cells were confirmed by a combination of RT-PCR, cloning and DNA sequencing.

To determine whether the pphK2 protein is expressed in the insect cell Sf9, time course studies using $^{35}$S-labeling of de novo synthesis of protein was performed and detected by SDS denaturing polyacrylamide gel electrophoresis (PAGE). As seen in the autoradiograph (FIG. 1), a unique protein (about 28 KDa) was found in pphK2-recombinant virus-infected Sf9 cells at 35–74 hour post-infection. This band was missing in uninfected cells or cells infected with wild type virus. The viral polyhedron protein (about 32 KDa) was found (FIG. 1) as expected in Sf9 cells infected with wild type virus, whereas it was not expressed by recombinant virus (FIG. 1). The protein was detected in cytosol when subcellular fractions (cytosol vs. insoluble fraction) was prepared by lysing cells with $H_2O$ and freeze-thaw, whereas this 28 KD protein was detected in insoluble fraction when prepared by a detergent buffer and freeze-thaw (data not shown).

Figure 2:
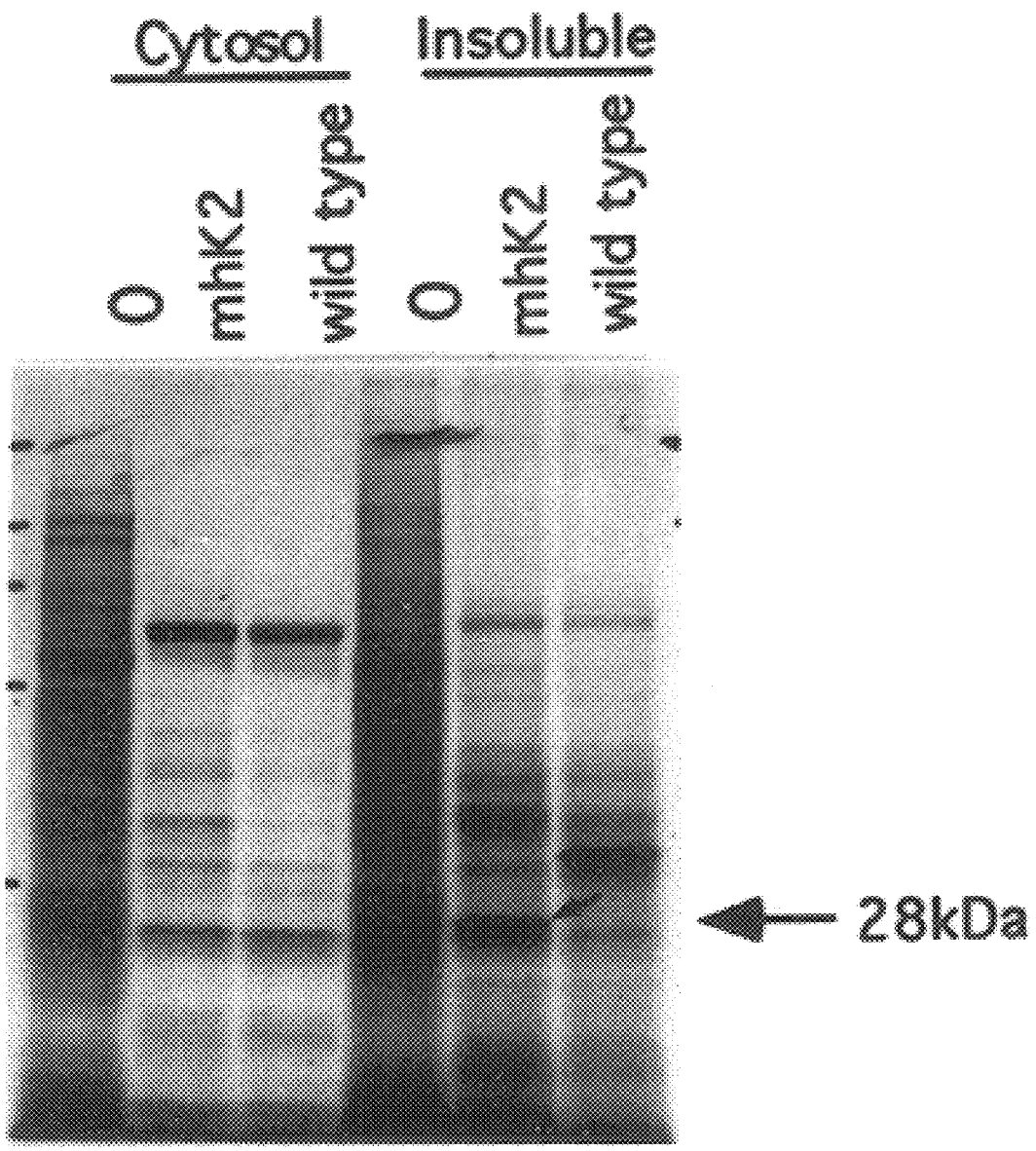
FIG. 2 depicts the detection of recombinant mhK2 in cell lysate fractions. S.f9 cells were infected either with recombinant mhK2, wild type or left uninfected for 48 hours. Methionine and cysteine pools were depleted for 1 hour in deficient media. Cells were supplemented with [$^{35}$S]-methionine and [$^{35}$S]-cysteine for 6 hours. Cells were separated into soluble and insoluble fractions using $H_2O$ and repeated freeze/thaw conditions. Aliquots of protein (50 $\mu$g per lane) were loaded onto a 10% Tris-Glycine SDS gel and electrophoresed. The gel was dried and exposed to x-ray film for 2 days. The band of interest is indicated with an arrow.

The mhK2 protein was also expressed in the insect cell Sf9, $^{35}$S-labeling of de novo synthesized protein was performed. As seen in the autoradiograph (FIG. 2), a unique protein (about 28 KDa) was found in the insoluble fraction of mhK2-recombinant virus-infected Sf9 cells at 48 hours post-infection. This band was missing in uninfected cells or cells infected with wild type virus. The viral polyhedron protein (about 32 KDa) was found in wild type virus-infected cells, whereas it was not expressed in cells infected with recombinant virus (FIG. 1). When the cytosol fraction was examined, no 28 KDa band was observed.

B. E. Coli system

Plasmid pBPPHK2 was transformed into E.coli BL21 (DE3) pLysS (Novagen, Inc., Madison, Wis.). This strain contains a chromosomal copy of T7 RNA polymerase under the control of inducible LacUV5 promoter. Upon addition of IPTG (isopropyl-β-D-thiogalactopyranoside) the expression of the T7 RNA polymerase is induced which in turn activates the T7 promoter resulting in overproduction of the gene product under control of this promoter. To determine whether the product of the ppHK2 gene would be expressed from pBPPHK2, single colonies of BL,21 E. Coli transformed with pBPPHK2 were grown to O.D.$_{600}$=0.2 in 10 ml LB media plus ampicillin (100μg/ml) and induced with 0.4 mM IPTG (Sigma, Inc.). Cells were harvested 2 hours after induction by centrifugation and resuspended in 1.5 ml SDS/PAGE sample buffer (U. K. Laemmli, Nature, 227, 680 1970) before SDS/PAGE analysis. The cell pellet from the IPTG-induced culture was resuspended in 0.05M Tris, pH 8.0 (at 9m/lgm cell pellet) and stirred at room temperature (25° C., r.t.) for 1 hour. Lysozyme (4 mg/ml) was added to this suspension (at 1 ml/gm cell pellet) and the suspension was stirred at r.t. for 30 min followed by incubation on ice for 30 min. The suspension was sonicated for 2 min at 150 watts and centrifuged at 3000×g to isolate the inclusion bodies. Inclusion bodies were resuspended in running buffer (25 mM Tris, 192 mM glycine, 0.1% SDS) and after centrifugation both the pellet and the supernatant were analyzed by SDS/PAGE.

About 90% of the pphK2 was found to be in the supernatant fraction which indicated that pphK2 is soluble in 0.1% SDS. To prepare samples for amino acid sequence analysis, 20,l of inclusion body lysate was subjected to SDS/PAGE on a 4–20% gradient gel (BIO-RAD, Inc., Melville, N.Y.). The protein was blotted from the gel onto 0.2 μPVDF paper (BIO-RAD) and stained with Coomassie blue. The protein band of interest was cut out from the blot and subjected to amino acid sequencing using a protein sequencer model 477A (Applied Biosystem, Inc., Foster City, Calif.).

Figure 3:
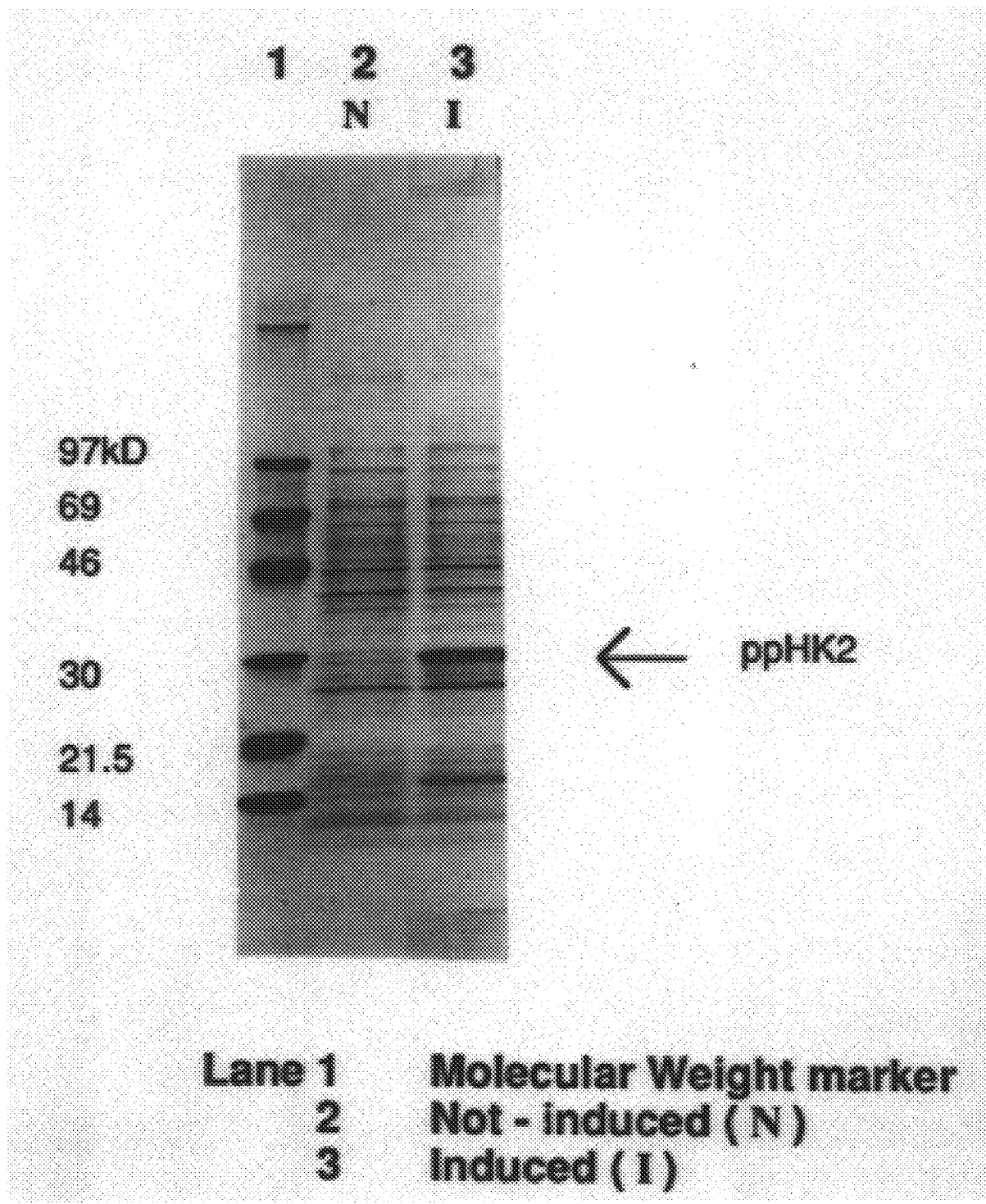
FIG. 3 depicts the expression of recombinant pphK2 in E. coli. E. coli strain BL21 (DE3) LysS harboring pBppHK2 was grown in LB media to $O.D._{600}$ 0.2 and incubated without (lane 2, not-induced (N)) or with (lane 3, induced (I)) 0.4 mM IPTG for 2 hrs. Cells were lysed in sample buffer and subjected to SDS/PAGE on a 4–20% gradient gel. Protein bands were visualized by staining the gel with Coomassie blue.

The induced cells overproduced large amounts of a polypeptide with apparent molecular mass of about 28kd (FIG. 3). Densitometric analysis indicated that this protein comprised approximately 40% of total cellular protein. The size of this protein as determined by an SDS-PAGE gel was comparable to that predicted from coding sequence for pphK2. To confirm that this protein is pphK2, the sequence of the first 10 amino acids (MWDLVLSLAL) (SEQ ID NO: 13) from the N-terminus was determined. This sequence agrees perfectly with that deduced from the DNA sequence of pphK2 cDNA. As noted, it has different identity from the first 10 amino acids of both pphK1 (MWFLVLCLAL) (SEQ ID NO: 14) and pphK3 (MWVPVVFLTL) (SEQ ID NO: 15). It also shows that this protein is not modified or processed at the N-terminus either during or after expression in E. coli. These results demonstrate that we were able to accurately express pphK2 in E.coli from pBPPHK2.

C. Mammalian System

1. Isolation and Purification of Protein

Figure 8:
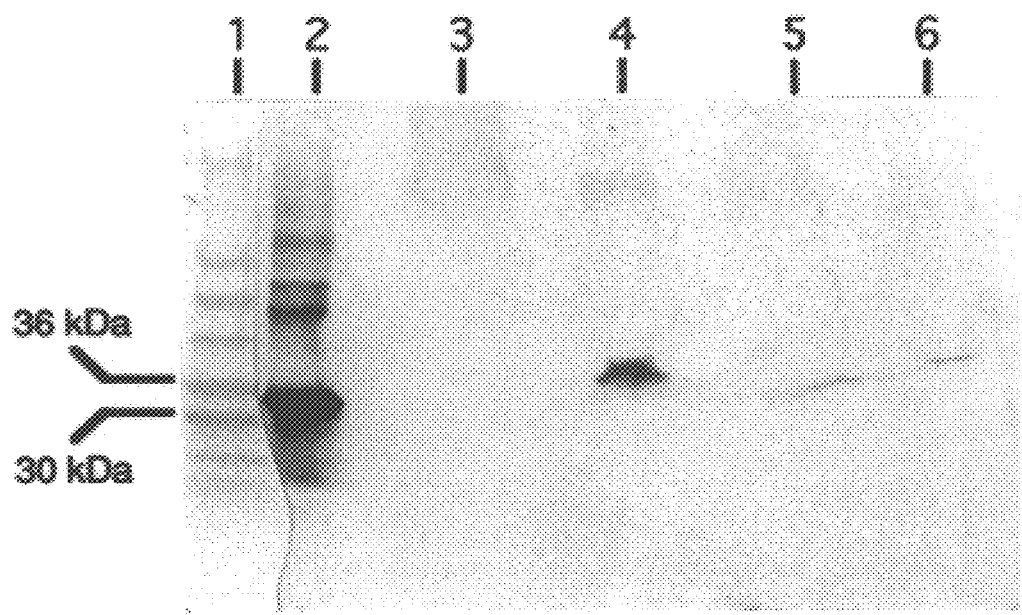
FIG. 8 depicts a gel confirming the expression of recombinant pphK2 in a mammalian cell line. AV12-pGThK2 (Lane 4–6) and AV12-pGT-d (Lane 3) clonal cell lines were grown in D F media. About 300$\mu$l of spent medium from the above clones were concentrated and subjected to SDS/PAGE along with See Blue MW marker (lane 1) and pphK2 lysate from E. coli cells (lane 2). The gel was blotted onto nitrocellulose paper and immunoblotted using a 1/1000dilution of anti-pphK2 rabbit antiserum. HRP-goat anti-rabbit was used as the secondary probe and the blot was developed by DAB plus $H_2 O_2$. Lane 3 (AV12-pGT-d) is AV12 transfected with vector without insert.

Plasmid pGThK2 was transformed into hamster cell line AV12–664 (ATCC-CRL-9595). To determine whether the product of the ppHK2 gene would be expressed from pGThK2, AV12-pGThK2#2 was grown in D10F +200nM MTX. At about 60% confluency the cells were washed with Hank's balanced salt solution and resuspended in serum-free HH4 medium. The spent medium was collected after 7 days (serum-free spent medium) and stored at −20° C. FIG. 8 depicts a SDS-PAGE confirming expression of recombinant pphK2 in a mammalian cell line. AV12-pGThK2 (Lane 4–6) and AV12-pGT-d (Lane 3) clonal cell lines were grown in D10F media. About 300μl of spent medium from the above clones were concentrated and subjected to SDS/PAGE along with See Blue MW marker (lane 1) and pphK2 lysate from E.coli cells (lane 2). The gel was blotted onto nitrocellulose paper and immunoblotted using a ¹⁄₁₀₀₀dilution of anti-pphK2 rabbit antiserum. HRP-goat anti-rabbit was used as the secondary probe and the blot was developed by DAB plus $H_2O_2$. Lane 3 (AV12-pGT-d) is AV12 transfected with vector without insert.

Figure 9:
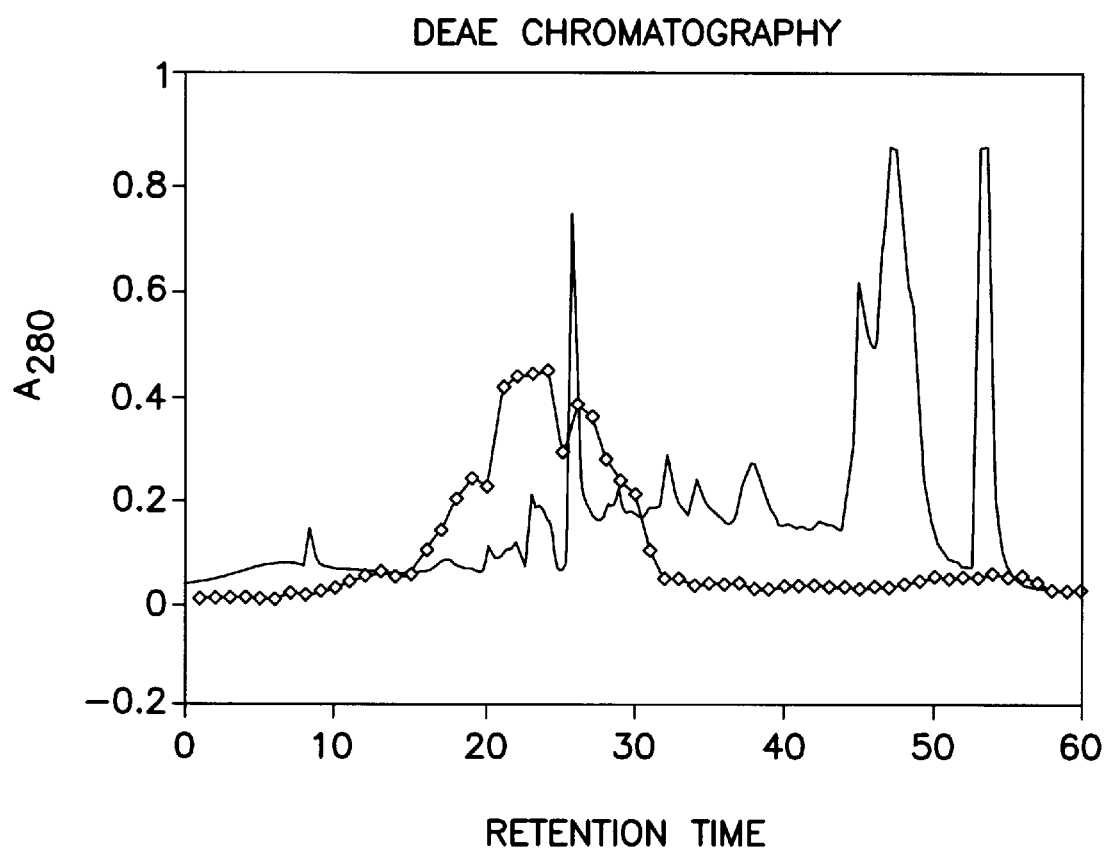
FIG. 9 depicts the DEAE chromatography of AV12 media. The sample was applied in a bicarbonte buffer, pH 8 and eluted with a salt gradient. The solid line is the $A_{280}$ elution profile. The diamond line represents the ELISA assay of individual samples which had been dried onto microtiter plates and developed with rabbit anti-hK2 antibody.

To purify the protein, the serum-free spent medium was concentrated from 5–10 fold by ultrafiltration with a 10 kDa molecular weight cutoff membrane then dialyzed overnight at 4° C. versus 50 mM sodium bicarbonate, pH 8. Samples were filtered with 0.2μ filters and then pumped directly onto a TSK DEAE-5PW HPLC column (21 mm ×150 mm) at a flow rate of 5 mL/min. Buffer A contained 50 mM sodium bicarbonate, pH 7.9 Buffer B contained 50 mM sodium bicarbonate plus 0.5 M sodium chloride, pH 7.6. The elution profile shown in FIG. 9 was developed with a gradient from 0–50% Buffer B over 35 min; 50–100% B from 35–40 min and isocratic elution at 100% B for 5 min before re-equilibration in Buffer A. The flow rate was SmL/min throughout.

DEAE fractions were assayed for the presence of hK2 by ELISA using rabbit anit-pphK2 as primary antibodies. The ELISA assayed showed a peak of hK2 activity which eluted at approximately 0–2M NaCl (shown as the triangle line in FIG. 9), which correlated well with the appearance of a 34 kDa band of protein seen by SDS-PAGE in the same fractions (data not shown).

Figure 10:
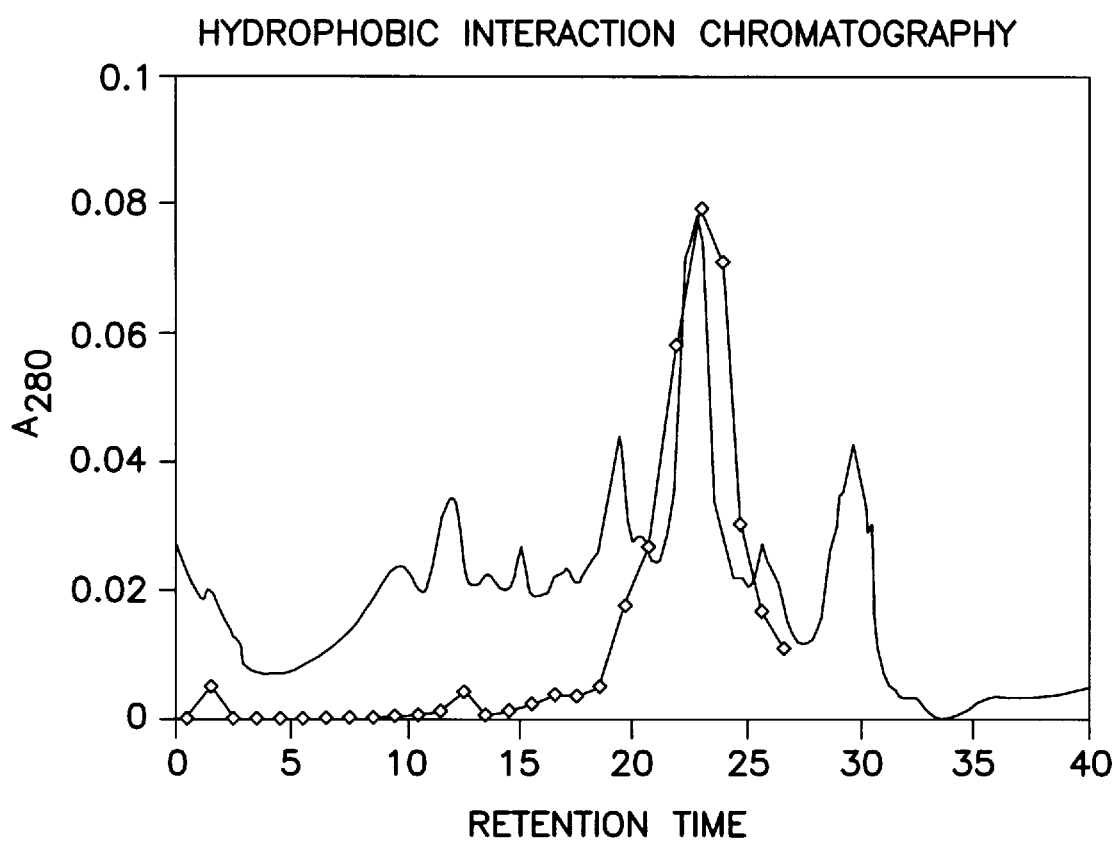
FIG. 10 depicts the hydrophobic interaction profile of DEAE fractions. The fractions were pooled, concentrated and applied to an HIC column in 1.2 M sodium sulfate, and eluted with a decreasing salt gradient. The solid line is $A_{280}$ and the diamond line shows the ELISA assay profile of the fractions using rabbit anti-hK2 antibody.

Fractions with hK2 activity were pooled and concentrated by ultrafiltration with 10 kDa membranes to approximately 5–8 mL where upon solid ammonium sulfate was added to make a final concentration of 1 M. This sample was then injected onto a PolyLC. polypropyl aspartamide column, 1000A pore size, 4.6 mm ×200 mm, to resolve protein by hydrophobic interaction chromatography (HIC, see FIG. 10). Buffer A was 20 mM Na phosphate, 1.2 M Na sulfate pH 6.3 and Buffer B was 50 mM Na phosphate, 5% 2-propanol, pH 7.4. The elution gradient was 0–20% B over 5 min; 20–55% B from 5–20 min, isocratic at 55% B from 20–23 min, 55–100% B from 23–25 min; isocratic at 100% B for 2 min before re-equilibration Buffer A. The flow rate was 0.7 mL/min. Greater than 90% of the $A_{280}$ was not retained on HIC column. The main peak retained on HIC, which eluted at 22 min, also showed the highest peak of activity by ELISA assay (triangle line, FIG. 10).

Figure 11:
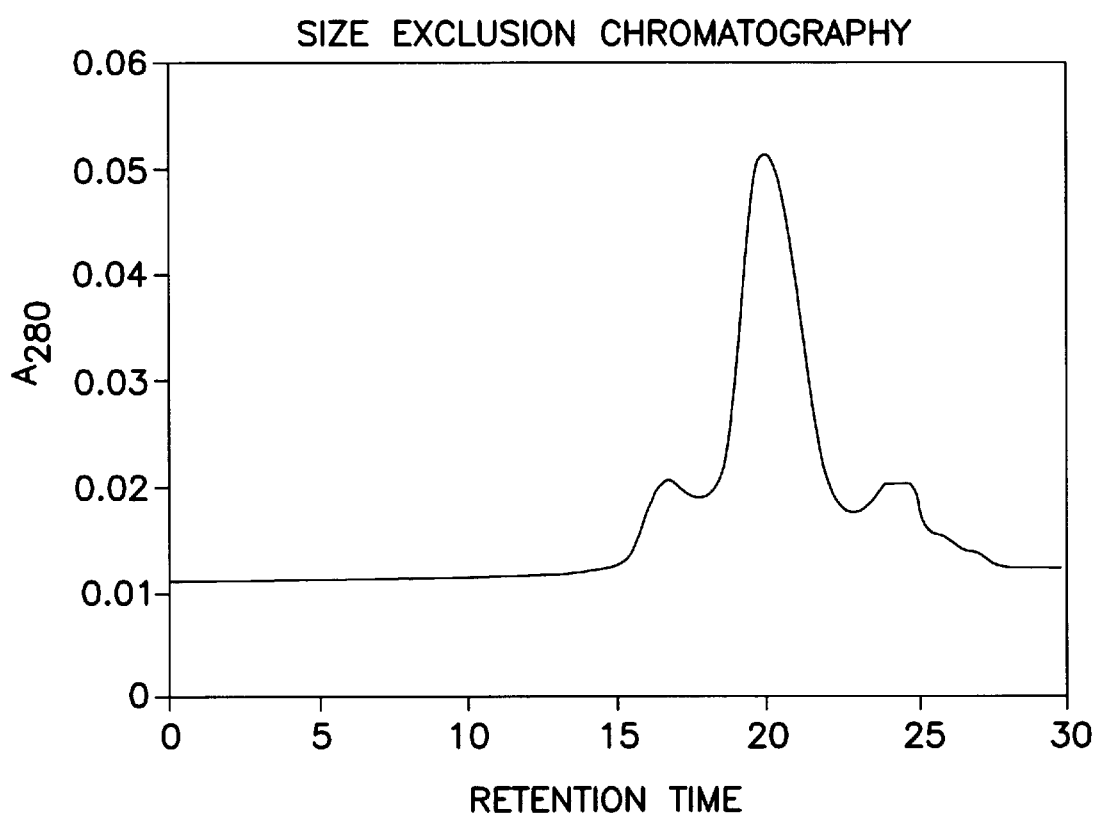
FIG. 11 depicts the Size Exclusion Chromatography of HIC purified prohK2, in particular, the $A_{280}$ profile of 22 min peak eluted off HIC column. The 19.4 min peak appears homogeneous by SDS-PAGE. After this peak was lyophilized, the N-terminal sequence and amino acid composition confirmed its identity as the pro form of hK2.

HIC fractions which tested positive for hK2 on ELISA were pooled, ultrafilter concentrated as above to a volume less than 1 mL then injected on a 10/30 Pharmacia S12 size exclusion column equilibrated in 100 mM ammonium acetate. The flow rate was 0.7 mL/min. When the 22 min peak from HIC was resolved by size exclusion chromatography, typically about 80–90% of the protein $A_{280}$ eluted at 19.4 min, a retention time consistent with a protein of approximately 34 kDa (FIG. 11). The only other protein peak on SEC, eluting at 16.7 min, corresponded to an about 70KDa protein seen also in previous purification steps.

Figure 12:
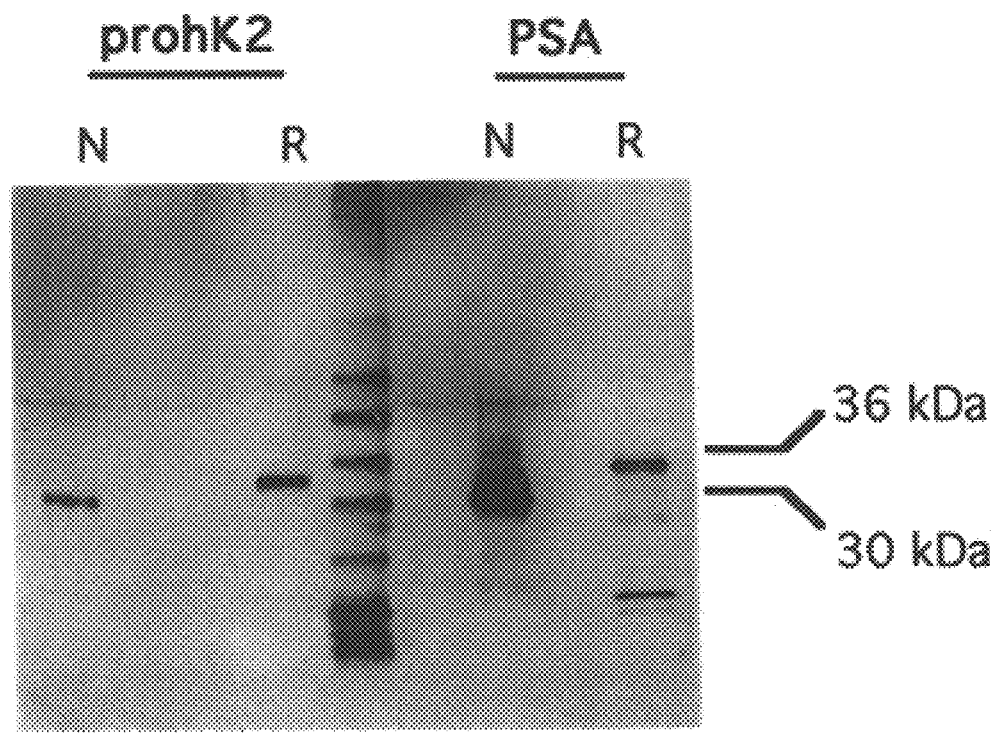
FIG. 12 depicts the SDS/PAGE analysis of prohK2 and PSA. 1.5µg of purified phK2 or PSA was boiled in sample buffer containing (R) or not containing (N) 1% BME. Samples were subjected to SDS/PAGE on a 4–20% gel. The protein bands were visualized by staining the gel with silver.

To examine the efficiency of our purification scheme, 1.5 μg of purified phK2 was subjected to SDS/PAGE in the presence or absence of β-mercaptoethanol (BME), and the gel was stained with silver. Results showed that the phK2 in our sample was about 95% pure (FIG. 12). It also showed that pro-hK2 migrated at about 30 KD in the absence of BME, and it migrated at about 34 kDa in the presence of BME. This pattern is similar to that observed for the PSA purified from seminal fluid (FIG. 12).

Recombinant phK2 is recognized by rabbit anti-pphK2, rabbit anti-PSA and a murine monoclonal antibody directed against a polypeptide covering amino acids 41–56 of hK2, when analyzed on WESTERN blots or when dried down on microtiter plates. However, phK2 was not detectable by these antibodies in sandwich assays. These results further demonstrate that the phK2 and PSA are conformationally different and the antibodies currently available to PSA or hK2 can not detect phK2 in its native form. Furthermore, phK2 was not detectable by the Tandem R or free-PSA assays (immunological assays for detection of PSA in serum).

A sample of the hybridoma (HK1A523.5) secreting the murine monoclonal antibody has been deposited in the American Type Culture Collection, Rockville, Md., and assigned ATCC HB-11876.

2. Amino Acid Analysis and Protein Sequencing of phK2

The peak collected off size exclusion chromatography (SEC) in ammonium acetate was lyophilized to remove the buffer then reconstituted in water. An aliquot (2.5μg)of this sample was loaded on a Porton membrane (Beckman instruments) and subjected to automated N-terminal sequence analysis on an Applied Biosystems model 477A protein sequencer which yielded the following sequence: Val-Pro-Leu-Ile-Gln-Ser-Arg-Ile-Val-Gly-Gly-Trp-Glu-(SEQ ID NO: 18). An aliquot of the same sample in water was also hydrolyzed in gaseous 6 N HCI under vacuum for 20 h at 112° C. then reconstituted in 0.1 IN HCI and analyzed on an Hewlett Packard Aminoquant amino acid analyzer utilizing pre-column derivatization of amino acids with OPA for primary and FMOC for secondary amines.

No competing sequence was evident from the profile of amino acids released sequentially by the Edman degradation procedure. By analogy to PSA this protein is pro hK2, since the known sequence of mature PSA has been shown to begin with Ileu-Val-Gly-etc and pro PSA has been postulated to have an extra 7 amino acids at the N-terminus. Amino acid analysis of this protein yielded an amino acid composition consistent with the recombinant sequence of prohK2. These results demonstrate that pphK2 having SEQ ID NO: 19 was accurately expressed in the mammalian cell line AV12–664 from pGThK2.

EXAMPLE 5.

Production of Antibodies to Recombinant pphK2
A. *E. Coli* System

To prepare pphK2 for rabbit immunization, the inclusion bodies obtained from bacterial cultures of BL21 (pBpphK2) after IPTG induction as in Example 4B were resuspended in 100μl SDS/PAGE sample buffer/ml bacterial culture and electrophoresed on preparative SDS/PAGE. The pphK2 band was excised and electroeluted from the gel into running buffer (25mM Tris, 192 mM glycine, 0.1% SDS) and used as the immunogen. Two rabbits were each immunized with 100μg of the immunogen in complete Freund's adjuvant and were boosted twice in three week intervals with 100μg of the immunogen in incomplete Freund's adjuvant and PBS, respectively. Rabbit anti-pphK2 sera was obtained one week following the second boost. The presence of anti-pphK2 in the rabbit antiserum was shown by ELISA (data not shown). Once confirmed by this method, the highest titer antiserum was tested on Western blots using lysates from IPTG induced or non-induced cultures of Bl.21 (pBpphK2). It was evident that the antiserum contained antibodies highly specific for the pphK2 protein since a protein band at about 28kd corresponding to pphK2 was recognized only in the induced lysate. The antiserum also recognized the purified pphK2 further showing the specificity of the antibodies to pphK2. The above data demonstrate that the antibodies recognize the prepro-form of hK2.

To delineate if the antiserum recognizes the mature form of hK2 (mhK2), mhK2 was expressed in *E.coli* as a glutathione S-transferase fusion protein (GST-mhK2, 58kd), and the cell lysate was immunoblotted using anit-pphK2 rabbit antiserum. It was evident that anti-pphK2 antiserum recognized the GST-mkK2, demonstrating that antibodies were at least in part against the mature region of pphK2. To examine the pattern recognized in seminal fluid by anti-pphK2 antibodies, seminal fluid was prepared from pooled semen as described by Sensabaugh and Blake, *J. Urology*, 149, 1523 (1990), and immunoblotted with anti-pphK2 rabbit antiserum. The antiserum recognized a major band at about 34kd plus several minor bands at lower MW. The pre-immune serum did not recognize any bands in any of the above experiments, showing that the antibodies were generated by immunization.

To determine whether there are any pphK2-specific antibodies in rabbit anit-pphK2 antiserum, the antibodies cross-reacting to PSA were absorbed out of the antiserum by a PSA affinity resin. Specifically, 1 m of the sera was diluted with in 1mL 100 mM HEPES, pH.7.5 and incubated with native PSA-bound Affigel-10 for 3.5 hours at 4° C. The mixture was used poured into a column, the flow-through was collected and the column was washed with 30 ml HEPES buffer. Antibodies bound to the column (eluate) were eluted by acetic acid (1N, pH 4.0) and neutralized to pH.6.6 with $NH_4OH$. Native PSA was isolated from seminal fluid as described by Sensabaugh and Blake, cited above. ppPSA was purified from *E.coli* transformed with plasmid pPHS579 (containing ppPSA under control of T7 promoter) using a procedure analogous to pphK2 purification.

The flow-through and the column eluate were tested for Abs recognizing pphK2, ppPSA and native PSA (PSA isolated from seminal fluid) using Western blot analysis. It was evident that antibodies in the untreated rabbit anti-pphK2 antiserum recognized all three proteins indicating that pphK2, ppPSA and seminal fluid-PSA share some similar epitopes. However, while the column eluate contained antibodies that recognized all three protein, the flow-through contained antibodies that recognized only pphK2. This indicates that anti-pphK2 antiserum contains pphK2-specific antibodies and these antibodies can be isolated by PSA affinity absorption. This system enabled us to generate anti-pphK2 antibodies which recognize both pphK2 and mhK2. Thus, utilizing immunogenic and pure recombinant hK2 protein, generate rabbit antiserum was generated which contains pphK2-specific antibodies, providing a valuable source for generating and screening for hK2-specific monoclonal antibodies.

These examples describe the use of three heterologous expression systems (i.e. both prokaryotic and eukaryotic) for the successful expression of the hK2 polypeptide. Thus, the method of the invention enables production of large quantities of substantially pure hK2 polypeptide. The polypeptide can be used both to study its biological functions and to produce immunodetection reagents such as labelled hK2 polypeptide, labelled fragments thereof and antibodies thereto. The immunoreagents can provide a method to purify native hK2 and to study the properties of the purified native hK2 polypeptide.

The pphK2 overproduced in *E.coli* can be readily solubilized in 0.1% SDS, thus solubility is not a problem. This is in contrast to the expression of human salivary kallikrein protein, hK1, in *E. coli*, which was found in insoluble inclusion bodies (J. Wang, et al *Biochem. J.*, 276,63 (1991)). In contrast, the present invehomogeneity balmost pure protein which can be purified to homogeneity by preparative SDS-PAGE. This purified recombinant pphK2 can be used for the generation of monoclonal and polyclonal antibodies.

As shown above, Baculogold viral DNA can be used to generate a recombinant baculovirus containing pphK2 or mhK2. Use of Baculogold viral DNA provides high selection of positive recombinant baculoviruses. Indeed, Northern blot analysis showed a high frequency of recombinant virus expressing pphK2 or mhK2 mRNA. Moreover, SDS-PAGE analysis showed that both pphK2 and mhK2 recombinant viruses produced unique proteins with sizes similar to the calculated molecular weights for pphK2 or mhK2. Although the levels of the recombinant hK2 expressed in insect system may not be as high as in *E. coli*, the hK2 protein produced in baculovirus-insect system may contain the secreted form which would be more like the natural form of the protein.

Plasmids pphK2/pVL1393 in E. col. H13101 has been deposited in the American Type Culture Collection, Rockville, Md., USA on May 2, 1994 under the provisions of the Budapest Treaty and have been assigned accession number ATCC 69614.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated nucleic acid molecule encoding a variant pre-pro hK2 polypeptide, a variant pro hK2 polypeptide, or a variant mature hK2 polypeptide, wherein the variant hK2 polypeptide has at least one amino acid at amino acid positions 1–14, 27–40, 57–152 or 168–237 substituted relative to SEQ ID NO: 16, and 100% sequence identity to acid sequence corresponding to SEQ ID NO: 16 at amino acid positions 15–26, 41–56 and 153–167 of SEQ ID NO: 16, wherein the variant polypeptide binds to an antibody that binds to mature hK2 but not to PSA.

2. An isolated nucleic acid molecule comprising SEQ ID NO:20.

3. The nucleic acid molecule of claim 1 or 2 further comprising a promoter operably linked to the nucleic acid molecule.

4. An expression vector comprising the nucleic acid molecule of claim 1 or 2 operably linked to control sequences recognized by a host cell transformed with the vector.

5. The vector of claim 4 wherein the host cell is a bacterial host cell.

6. The vector of claim 4 wherein the host cell is a mammalian cell.

7. A host cell transformed with the vector of claim 4.

8. The host cell of claim 7 which is a bacterial host cell.

9. The host cell of claim 7 which is a mammalian host cell.

10. A method of using a nucleic acid molecule encoding a hK2 polypeptide comprising expressing the nucleic acid molecule of claim 1 or 2 in a cultured host cell stably transformed with a vector comprising said nucleic acid molecule operably linked to control sequences recognized by the host cell transformed with the vector, and recovering hK2 polypeptide from the host cell.

11. The method of claim 10 wherein the host cell is a bacterial host cell.

12. The method of claim 10 wherein the host cell is a mammalian host cell.

13. The method of claim 10 wherein the nucleic acid molecule is DNA.

14. The method of claim 10 wherein the hK2 polypeptide is recovered from the host cell culture medium.

15. The vector of claim 4 wherein the host cell is an insect cell.

16. The host cell of claim 7 which is an insect host cell.

17. The method of claim 10 wherein the host cell is an insect cell.

* * * * *

UNITED STATES PATENT AND TRADEMARK OFFICE
CERTIFICATE OF CORRECTION

PATENT NO.: 6,013,471
DATED: Jan. 11, 2000
INVENTOR(S): Tindall et al.

It is certified that error appears in the above-identified patent and that said Letters Patent is hereby corrected as shown below:

In column 2, line 46, delete "or SEQ ID NO:20" and insert --, SEQ ID NO:9 or SEQ ID NO: 20--, therefor.

In column 4, line 49, delete "D F media" and insert --D10F media--, therefor.

In column 5, line 63, delete "an later" and insert --and later--, therefor.

In column 10, line 53, delete "prepared" and insert --preparing--, therefor.

In column 12, line 24, delete "NO: 17)" and insert --NO: 17--, therefor.

In column 12, line 38, delete "within" and insert --with--, therefor.

In column 12, line 39, delete "plasinid" and insert --plasmid--, therefor.

In column 16, line 18, delete "0.1 IN HCI" and insert --0.1 N HCl--, therefor.

In column 17, line 15, delete "with in" and insert --with--, therefor.

In column 18, line 15, delete "invehomogeneity balmost" and insert --invention yields almost--, therefor.

Signed and Sealed this

First Day of May, 2001

Attest:

NICHOLAS P. GODICI

*Attesting Officer*   *Acting Director of the United States Patent and Trademark Office*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

```
Ile Val Gly Gly Trp Glu Cys Glu Lys His Ser Gln Pro Trp Gln Val
1               5                   10                  15
```

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
            35                  40                  45

Ile Leu Leu Gly Arg His Ser Leu Phe His Pro Glu Asp Thr Gly Gln
50                      55                  60

Val Phe Gln Val Ser His Ser Phe Pro His Pro Leu Tyr Asp Met Ser
65                      70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
            115                 120                 125

Tyr Ala Ser Gly Trp Gly Ser Ile Glu Pro Glu Glu Phe Leu Thr Pro
            130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
            195                 200                 205

Pro Cys Ala Leu Pro Glu Arg Pro Ser Leu Tyr Thr Lys Val Val His
210                 215                 220

Tyr Arg Lys Trp Ile Lys Asp Thr Ile Val Ala Asn Pro
225                 230                 235

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ACGCGGATCC AGCATGTGGG ACCTGGTTCT CT                              32

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ACAGCTGCAG TTTACTAGAG GTAGGGGTGG GAC                             33

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ACCGGAATTC ATGATTGTGG GAGGCTGGGA GTGT    34

(2) INFORMATION FOR SEQ ID NO:5:

(i) SEQUENCE CHARACTERISTICS:
        (A) LENGTH: 832 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 10..792

(xi) SEQUENCE DESCRIPTION: SEQ ID NO:5:

```
GGATCCAGC ATG TGG GAC CTG GTT CTC TCC ATC GCC TTG TCT GTG GGG        48
          Met Trp Asp Leu Val Leu Ser Ile Ala Leu Ser Val Gly
            1               5                  10

TGC ACT GGT GCC GTG CCC CTC ATC CAG TCT CGG ATT GTG GGA GGC TGG      96
Cys Thr Gly Ala Val Pro Leu Ile Gln Ser Arg Ile Val Gly Gly Trp
 15                  20                  25

GAG TGT GAG AAG CAT TCC CAA CCC TGG CAG GTG GCT GTG TAC AGT CAT     144
Glu Cys Glu Lys His Ser Gln Pro Trp Gln Val Ala Val Tyr Ser His
 30                  35                  40                  45

GGA TGG GCA CAC TGT GGG GGT GTC CTG GTG CAC CCC CAG TGG GTG CTC     192
Gly Trp Ala His Cys Gly Gly Val Leu Val His Pro Gln Trp Val Leu
                 50                  55                  60

ACA GCT GCC CAT TGC CTA AAG AAG AAT AGC CAG GTC TGG CTG GGT CGG     240
Thr Ala Ala His Cys Leu Lys Lys Asn Ser Gln Val Trp Leu Gly Arg
                 65                  70                  75

CAC AAC CTG TTT GAG CCT GAA GAC ACA GGC CAG AGG GTC CCT GTC AGC     288
His Asn Leu Phe Glu Pro Glu Asp Thr Gly Gln Arg Val Pro Val Ser
             80                  85                  90

CAC AGC TTC CCA CAC CCG CTC TAC AAT ATG AGC CTT CTG AAG CAT CAA     336
His Ser Phe Pro His Pro Leu Tyr Asn Met Ser Leu Leu Lys His Gln
         95                 100                 105

AGC CTT AGA CCA GAT GAA GAC TCC AGC CAT GAC CTC ATG CTG CTC CGC     384
Ser Leu Arg Pro Asp Glu Asp Ser Ser His Asp Leu Met Leu Leu Arg
110                 115                 120                 125

CTG TCA GAG CCT GCC AAG ATC ACA GAT GTT GTG AAG GTC CTG GGC CTG     432
Leu Ser Glu Pro Ala Lys Ile Thr Asp Val Val Lys Val Leu Gly Leu
                130                 135                 140

CCC ACC CAG GAG CCA GCA CTG GGG ACC ACC TGC TAC GCC TCA GGC TGG     480
Pro Thr Gln Glu Pro Ala Leu Gly Thr Thr Cys Tyr Ala Ser Gly Trp
                145                 150                 155

GGC AGC ATC GAA CCA GAG GAG TTC TTG CGC CCC AGG AGT CTT CAG TGT     528
Gly Ser Ile Glu Pro Glu Glu Phe Leu Arg Pro Arg Ser Leu Gln Cys
            160                 165                 170

GTG AGC CTC CAT CTC CTG TCC AAT GAC ATG TGT GCT AGA GCT TAC TCT     576
Val Ser Leu His Leu Leu Ser Asn Asp Met Cys Ala Arg Ala Tyr Ser
        175                 180                 185

GAG AAG GTG ACA GAG TTC ATG TTG TGT GCT GGG CTC TGG ACA GGT GGT     624
Glu Lys Val Thr Glu Phe Met Leu Cys Ala Gly Leu Trp Thr Gly Gly
190                 195                 200                 205

AAA GAC ACT TGT GGG GGT GAT TCT GGG GGT CCA CTT GTC TGT AAT GGT     672
Lys Asp Thr Cys Gly Gly Asp Ser Gly Gly Pro Leu Val Cys Asn Gly
                210                 215                 220
```

```
GTG CTT CAA GGT ATC ACA TCA TGG GGC CCT GAG CCA TGT GCC CTG CCT    720
Val Leu Gln Gly Ile Thr Ser Trp Gly Pro Glu Pro Cys Ala Leu Pro
        225                 230                 235

GAA AAG CCT GCT GTG TAC ACC AAG GTG GTG CAT TAC CGG AAG TGG ATC    768
Glu Lys Pro Ala Val Tyr Thr Lys Val Val His Tyr Arg Lys Trp Ile
    240                 245                 250

AAG GAC ACC ATC GCA GCC AAC CCC TGAGTGCCCC TGTCCCACCC CTACCTCTAG    822
Lys Asp Thr Ile Ala Ala Asn Pro
    255                 260

TAAACTGCAG                                                          832

(2) INFORMATION FOR SEQ ID NO:6:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:6:

Met Trp Asp Leu Val Leu Ser Ile Ala Leu Ser Val Gly Cys Thr Gly
 1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

(2) INFORMATION FOR SEQ ID NO:7:
```

(i) SEQUENCE CHARACTERISTICS:
    (A) LENGTH: 760 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 7..720

(xi) SEQUENCE DESCRIPTION: SEQ ID NO:7:

```
GAATTC ATG ATT GTG GGA GGC TGG GAG TGT GAG AAG CAT TCC CAA CCC        48
       Met Ile Val Gly Gly Trp Glu Cys Glu Lys His Ser Gln Pro
       1               5                   10

TGG CAG GTG GCT GTG TAC AGT CAT GGA TGG GCA CAC TGT GGG GGT GTC       96
Trp Gln Val Ala Val Tyr Ser His Gly Trp Ala His Cys Gly Gly Val
15                  20                  25                  30

CTG GTG CAC CCC CAG TGG GTG CTC ACA GCT GCC CAT TGC CTA AAG AAG      144
Leu Val His Pro Gln Trp Val Leu Thr Ala Ala His Cys Leu Lys Lys
                35                  40                  45

AAT AGC CAG GTC TGG CTG GGT CGG CAC AAC CTG TTT GAG CCT GAA GAC      192
Asn Ser Gln Val Trp Leu Gly Arg His Asn Leu Phe Glu Pro Glu Asp
            50                  55                  60

ACA GGC CAG AGG GTC CCT GTC AGC CAC AGC TTC CCA CAC CCG CTC TAC      240
Thr Gly Gln Arg Val Pro Val Ser His Ser Phe Pro His Pro Leu Tyr
        65                  70                  75

AAT ATG AGC CTT CTG AAG CAT CAA AGC CTT AGA CCA GAT GAA GAC TCC      288
Asn Met Ser Leu Leu Lys His Gln Ser Leu Arg Pro Asp Glu Asp Ser
    80                  85                  90

AGC CAT GAC CTC ATG CTG CTC CGC CTG TCA GAG CCT GCC AAG ATC ACA      336
Ser His Asp Leu Met Leu Leu Arg Leu Ser Glu Pro Ala Lys Ile Thr
95                  100                 105                 110

GAT GTT GTG AAG GTC CTG GGC CTG CCC ACC CAG GAG CCA GCA CTG GGG      384
Asp Val Val Lys Val Leu Gly Leu Pro Thr Gln Glu Pro Ala Leu Gly
                115                 120                 125

ACC ACC TGC TAC GCC TCA GGC TGG GGC AGC ATC GAA CCA GAG GAG TTC      432
Thr Thr Cys Tyr Ala Ser Gly Trp Gly Ser Ile Glu Pro Glu Glu Phe
            130                 135                 140

TTG CGC CCC AGG AGT CTT CAG TGT GTG AGC CTC CAT CTC CTG TCC AAT      480
Leu Arg Pro Arg Ser Leu Gln Cys Val Ser Leu His Leu Leu Ser Asn
        145                 150                 155

GAC ATG TGT GCT AGA GCT TAC TCT GAG AAG GTG ACA GAG TTC ATG TTG      528
Asp Met Cys Ala Arg Ala Tyr Ser Glu Lys Val Thr Glu Phe Met Leu
    160                 165                 170

TGT GCT GGG CTC TGG ACA GGT GGT AAA GAC ACT TGT GGG GGT GAT TCT      576
Cys Ala Gly Leu Trp Thr Gly Gly Lys Asp Thr Cys Gly Gly Asp Ser
175                 180                 185                 190

GGG GGT CCA CTT GTC TGT AAT GGT GTG CTT CAA GGT ATC ACA TCA TGG      624
Gly Gly Pro Leu Val Cys Asn Gly Val Leu Gln Gly Ile Thr Ser Trp
                195                 200                 205

GGC CCT GAG CCA TGT GCC CTG CCT GAA AAG CCT GCT GTG TAC ACC AAG      672
Gly Pro Glu Pro Cys Ala Leu Pro Glu Lys Pro Ala Val Tyr Thr Lys
            210                 215                 220

GTG GTG CAT TAC CGG AAG TGG ATC AAG GAC ACC ATC GCA GCC AAC CCC      720
Val Val His Tyr Arg Lys Trp Ile Lys Asp Thr Ile Ala Ala Asn Pro
        225                 230                 235

TGAGTGCCCC TGTCCCACCC CTACCTCTAG TAAACTGCAG                          760
```

(2) INFORMATION FOR SEQ ID NO:8:

(i) SEQUENCE CHARACTERISTICS:

(A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:8:

Met Ile Val Gly Gly Trp Glu Cys Glu Lys His Ser Gln Pro Trp Gln
 1               5                  10                  15

Val Ala Val Tyr Ser His Gly Trp Ala His Cys Gly Gly Val Leu Val
             20                  25                  30

His Pro Gln Trp Val Leu Thr Ala Ala His Cys Leu Lys Lys Asn Ser
         35                  40                  45

Gln Val Trp Leu Gly Arg His Asn Leu Phe Glu Pro Glu Asp Thr Gly
     50                  55                  60

Gln Arg Val Pro Val Ser His Ser Phe Pro His Pro Leu Tyr Asn Met
65                  70                  75                  80

Ser Leu Leu Lys His Gln Ser Leu Arg Pro Asp Glu Asp Ser Ser His
                 85                  90                  95

Asp Leu Met Leu Leu Arg Leu Ser Glu Pro Ala Lys Ile Thr Asp Val
            100                 105                 110

Val Lys Val Leu Gly Leu Pro Thr Gln Glu Pro Ala Leu Gly Thr Thr
        115                 120                 125

Cys Tyr Ala Ser Gly Trp Gly Ser Ile Glu Pro Glu Glu Phe Leu Arg
    130                 135                 140

Pro Arg Ser Leu Gln Cys Val Ser Leu His Leu Leu Ser Asn Asp Met
145                 150                 155                 160

Cys Ala Arg Ala Tyr Ser Glu Lys Val Thr Glu Phe Met Leu Cys Ala
                165                 170                 175

Gly Leu Trp Thr Gly Gly Lys Asp Thr Cys Gly Gly Asp Ser Gly Gly
            180                 185                 190

Pro Leu Val Cys Asn Gly Val Leu Gln Gly Ile Thr Ser Trp Gly Pro
        195                 200                 205

Glu Pro Cys Ala Leu Pro Glu Lys Pro Ala Val Tyr Thr Lys Val Val
    210                 215                 220

His Tyr Arg Lys Trp Ile Lys Asp Thr Ile Ala Ala Asn Pro
225                 230                 235

(2) INFORMATION FOR SEQ ID NO:9:

(i) SEQUENCE CHARACTERISTICS:
        (A) LENGTH: 766 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..732

(xi) SEQUENCE DESCRIPTION: SEQ ID NO:9:

GTG CCC CTC ATC CAG TCT CGG ATT GTG GGA GGC TGG GAG TGT GAG AAG        48
Val Pro Leu Ile Gln Ser Arg Ile Val Gly Gly Trp Glu Cys Glu Lys
 1               5                  10                  15

CAT TCC CAA CCC TGG CAG GTG GCT GTG TAC AGT CAT GGA TGG GCA CAC        96
His Ser Gln Pro Trp Gln Val Ala Val Tyr Ser His Gly Trp Ala His
             20                  25                  30

TGT GGG GGT GTC CTG GTG CAC CCC CAG TGG GTG CTC ACA GCT GCC CAT       144
Cys Gly Gly Val Leu Val His Pro Gln Trp Val Leu Thr Ala Ala His

|   |   |   |   |   |   |   |   |   |   |   |   |   |   |   |   |
|---|---|---|---|---|---|---|---|---|---|---|---|---|---|---|---|
|   |   | 35 |   |   |   | 40 |   |   |   |   | 45 |   |   |   |   |
| TGC | CTA | AAG | AAG | AAT | AGC | CAG | GTC | TGG | CTG | GGT | CGG | CAC | AAC | CTG | TTT | 192 |
| Cys | Leu | Lys | Lys | Asn | Ser | Gln | Val | Trp | Leu | Gly | Arg | His | Asn | Leu | Phe |   |
|   |   | 50 |   |   |   | 55 |   |   |   |   | 60 |   |   |   |   |
| GAG | CCT | GAA | GAC | ACA | GGC | CAG | AGG | GTC | CCT | GTC | AGC | CAC | AGC | TTC | CCA | 240 |
| Glu | Pro | Glu | Asp | Thr | Gly | Gln | Arg | Val | Pro | Val | Ser | His | Ser | Phe | Pro |   |
| 65 |   |   |   | 70 |   |   |   |   | 75 |   |   |   |   | 80 |   |
| CAC | CCG | CTC | TAC | AAT | ATG | AGC | CTT | CTG | AAG | CAT | CAA | AGC | CTT | AGA | CCA | 288 |
| His | Pro | Leu | Tyr | Asn | Met | Ser | Leu | Leu | Lys | His | Gln | Ser | Leu | Arg | Pro |   |
|   |   |   |   | 85 |   |   |   |   | 90 |   |   |   |   | 95 |   |
| GAT | GAA | GAC | TCC | AGC | CAT | GAC | CTC | ATG | CTG | CTC | CGC | CTG | TCA | GAG | CCT | 336 |
| Asp | Glu | Asp | Ser | Ser | His | Asp | Leu | Met | Leu | Leu | Arg | Leu | Ser | Glu | Pro |   |
|   |   |   | 100 |   |   |   |   | 105 |   |   |   |   | 110 |   |   |
| GCC | AAG | ATC | ACA | GAT | GTT | GTG | AAG | GTC | CTG | GGC | CTG | CCC | ACC | CAG | GAG | 384 |
| Ala | Lys | Ile | Thr | Asp | Val | Val | Lys | Val | Leu | Gly | Leu | Pro | Thr | Gln | Glu |   |
|   |   | 115 |   |   |   |   | 120 |   |   |   |   | 125 |   |   |   |
| CCA | GCA | CTG | GGG | ACC | ACC | TGC | TAC | GCC | TCA | GGC | TGG | GGC | AGC | ATC | GAA | 432 |
| Pro | Ala | Leu | Gly | Thr | Thr | Cys | Tyr | Ala | Ser | Gly | Trp | Gly | Ser | Ile | Glu |   |
|   | 130 |   |   |   |   | 135 |   |   |   |   | 140 |   |   |   |   |
| CCA | GAG | GAG | TTC | TTG | CGC | CCC | AGG | AGT | CTT | CAG | TGT | GTG | AGC | CTC | CAT | 480 |
| Pro | Glu | Glu | Phe | Leu | Arg | Pro | Arg | Ser | Leu | Gln | Cys | Val | Ser | Leu | His |   |
| 145 |   |   |   |   | 150 |   |   |   |   | 155 |   |   |   |   | 160 |
| CTC | CTG | TCC | AAT | GAC | ATG | TGT | GCT | AGA | GCT | TAC | TCT | GAG | AAG | GTG | ACA | 528 |
| Leu | Leu | Ser | Asn | Asp | Met | Cys | Ala | Arg | Ala | Tyr | Ser | Glu | Lys | Val | Thr |   |
|   |   |   |   | 165 |   |   |   |   | 170 |   |   |   |   | 175 |   |
| GAG | TTC | ATG | TTG | TGT | GCT | GGG | CTC | TGG | ACA | GGT | GGT | AAA | GAC | ACT | TGT | 576 |
| Glu | Phe | Met | Leu | Cys | Ala | Gly | Leu | Trp | Thr | Gly | Gly | Lys | Asp | Thr | Cys |   |
|   |   |   | 180 |   |   |   |   | 185 |   |   |   |   | 190 |   |   |
| GGG | GGT | GAT | TCT | GGG | GGT | CCA | CTT | GTC | TGT | AAT | GGT | GTG | CTT | CAA | GGT | 624 |
| Gly | Gly | Asp | Ser | Gly | Gly | Pro | Leu | Val | Cys | Asn | Gly | Val | Leu | Gln | Gly |   |
|   |   | 195 |   |   |   |   | 200 |   |   |   |   | 205 |   |   |   |
| ATC | ACA | TCA | TGG | GGC | CCT | GAG | CCA | TGT | GCC | CTG | CCT | GAA | AAG | CCT | GCT | 672 |
| Ile | Thr | Ser | Trp | Gly | Pro | Glu | Pro | Cys | Ala | Leu | Pro | Glu | Lys | Pro | Ala |   |
|   | 210 |   |   |   |   | 215 |   |   |   |   | 220 |   |   |   |   |
| GTG | TAC | ACC | AAG | GTG | GTG | CAT | TAC | CGG | AAG | TGG | ATC | AAG | GAC | ACC | ATC | 720 |
| Val | Tyr | Thr | Lys | Val | Val | His | Tyr | Arg | Lys | Trp | Ile | Lys | Asp | Thr | Ile |   |
| 225 |   |   |   |   | 230 |   |   |   |   | 235 |   |   |   |   | 240 |
| GCA | GCC | AAC | CCC | TGAGTGCCCC | TGTCCCACCC | CTACCTCTAG | TAAA |   |   |   |   |   |   |   |   | 766 |
| Ala | Ala | Asn | Pro |   |   |   |   |   |   |   |   |   |   |   |   |   |

(2) INFORMATION FOR SEQ ID NO:10:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO:10:

```
Val Pro Leu Ile Gln Ser Arg Ile Val Gly Gly Trp Glu Cys Glu Lys
 1               5                  10                  15

His Ser Gln Pro Trp Gln Val Ala Val Tyr Ser His Gly Trp Ala His
                20                  25                  30

Cys Gly Gly Val Leu Val His Pro Gln Trp Val Leu Thr Ala Ala His
            35                  40                  45

Cys Leu Lys Lys Asn Ser Gln Val Trp Leu Gly Arg His Asn Leu Phe
        50                  55                  60

Glu Pro Glu Asp Thr Gly Gln Arg Val Pro Val Ser His Ser Phe Pro
65                  70                  75                  80
```

-continued

```
His Pro Leu Tyr Asn Met Ser Leu Leu Lys His Gln Ser Leu Arg Pro
                85                  90                  95
Asp Glu Asp Ser Ser His Asp Leu Met Leu Leu Arg Leu Ser Glu Pro
            100                 105                 110
Ala Lys Ile Thr Asp Val Val Lys Val Leu Gly Leu Pro Thr Gln Glu
        115                 120                 125
Pro Ala Leu Gly Thr Thr Cys Tyr Ala Ser Gly Trp Gly Ser Ile Glu
130                 135                 140
Pro Glu Glu Phe Leu Arg Pro Arg Ser Leu Gln Cys Val Ser Leu His
145                 150                 155                 160
Leu Leu Ser Asn Asp Met Cys Ala Arg Ala Tyr Ser Glu Lys Val Thr
                165                 170                 175
Glu Phe Met Leu Cys Ala Gly Leu Trp Thr Gly Gly Lys Asp Thr Cys
            180                 185                 190
Gly Gly Asp Ser Gly Gly Pro Leu Val Cys Asn Gly Val Leu Gln Gly
        195                 200                 205
Ile Thr Ser Trp Gly Pro Glu Pro Cys Ala Leu Pro Glu Lys Pro Ala
210                 215                 220
Val Tyr Thr Lys Val Val His Tyr Arg Lys Trp Ile Lys Asp Thr Ile
225                 230                 235                 240
Ala Ala Asn Pro
```

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TATACATATG TGGGACCTGG TTCTCTCC                                 28

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATATGGATCC TCAGGGGTTG GCTGCGATGG T                          31

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Met Trp Asp Leu Val Leu Ser Ile Ala Leu
1               5                   10
```

(2) INFORMATION FOR SEQ ID NO:14:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:14:

```
Met Trp Phe Leu Val Leu Cys Leu Ala Leu
 1               5                  10
```

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Met Trp Val Pro Val Val Phe Leu Thr Leu
 1               5                  10
```

(2) INFORMATION FOR SEQ ID NO:16:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ile Val Gly Gly Trp Glu Cys Glu Lys His Ser Gln Pro Trp Gln Val
 1               5                  10                  15

Ala Val Tyr Ser His Gly Trp Ala His Cys Gly Gly Val Leu Val His
                20                  25                  30

Pro Gln Trp Val Leu Thr Ala Ala His Cys Leu Lys Lys Asn Ser Gln
                35                  40                  45

Val Trp Leu Gly Arg His Asn Leu Phe Glu Pro Glu Asp Thr Gly Gln
 50                  55                  60

Arg Val Pro Val Ser His Ser Phe Pro His Pro Leu Tyr Asn Met Ser
 65                  70                  75                  80

Leu Leu Lys His Gln Ser Leu Arg Pro Asp Glu Asp Ser Ser His Asp
                85                  90                  95

Leu Met Leu Leu Arg Leu Ser Glu Pro Ala Lys Ile Thr Asp Val Val
                100                 105                 110

Lys Val Leu Gly Leu Pro Thr Gln Glu Pro Ala Leu Gly Thr Thr Cys
                115                 120                 125

Tyr Ala Ser Gly Trp Gly Ser Ile Glu Pro Glu Glu Phe Leu Arg Pro
                130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
                180                 185                 190

Leu Val Cys Asn Gly Val Leu Gln Gly Ile Thr Ser Trp Gly Pro Glu
```

```
                   195                 200                     205
Pro Cys Ala Leu Pro Glu Lys Pro Ala Val Tyr Thr Lys Val Val His
    210                 215                 220

Tyr Arg Lys Trp Ile Lys Asp Thr Ile Ala Ala Asn Pro
225                 230                 235
```

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
ATATGGATCC ATATGTCAGC ATGTGGGACC TGGTTCTCTC CA                              42
```

(2) INFORMATION FOR SEQ ID NO:18:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Val Pro Leu Ile Gln Ser Arg Ile Val Gly Gly Trp Glu
1               5                   10
```

(2) INFORMATION FOR SEQ ID NO:19:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:19:

```
Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
                20                  25                  30

Lys His Ser Gln Pro Trp Gln Val Ala Val Tyr Ser His Gly Trp Ala
            35                  40                  45

His Cys Gly Gly Val Leu Val His Pro Gln Trp Val Leu Thr Ala Ala
        50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160
```

-continued

```
Glu Pro Glu Glu Phe Leu Arg Pro Arg Ser Leu Gln Cys Val Ser Leu
            165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
            195                 200                 205

Cys Gly Gly Asp Ser Gly Gly Pro Leu Val Cys Asn Gly Val Leu Gln
210                 215                 220

Gly Ile Thr Ser Trp Gly Pro Glu Pro Cys Ala Leu Pro Glu Lys Pro
225                 230                 235                 240

Val Val Tyr Thr Lys Val Val His Tyr Arg Lys Trp Ile Lys Asp Thr
            245                 250                 255

Ile Ala Ala Asn Pro
            260
```

(2) INFORMATION FOR SEQ ID NO:20:

(i) SEQUENCE CHARACTERISTICS:
        (A) LENGTH: 832 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 10..792

(xi) SEQUENCE DESCRIPTION: SEQ ID NO:20:

```
GGATCCAGC ATG TGG GAC CTG GTT CTC TCC ATC GCC TTG TCT GTG GGG         48
          Met Trp Asp Leu Val Leu Ser Ile Ala Leu Ser Val Gly
          1               5                   10

TGC ACT GGT GCC GTG CCC CTC ATC CAG TCT CGG ATT GTG GGA GGC TGG       96
Cys Thr Gly Ala Val Pro Leu Ile Gln Ser Arg Ile Val Gly Gly Trp
15                  20                  25

GAG TGT GAG AAG CAT TCC CAA CCC TGG CAG GTG GCT GTG TAC AGT CAT      144
Glu Cys Glu Lys His Ser Gln Pro Trp Gln Val Ala Val Tyr Ser His
30                  35                  40                  45

GGA TGG GCA CAC TGT GGG GGT GTC CTG GTG CAC CCC CAG TGG GTG CTC      192
Gly Trp Ala His Cys Gly Gly Val Leu Val His Pro Gln Trp Val Leu
                50                  55                  60

ACA GCT GCC CAT TGC CTA AAG AAG AAT AGC CAG GTC TGG CTG GGT CGG      240
Thr Ala Ala His Cys Leu Lys Lys Asn Ser Gln Val Trp Leu Gly Arg
                65                  70                  75

CAC AAC CTG TTT GAG CCT GAA GAC ACA GGC CAG AGG GTC CCT GTC AGC      288
His Asn Leu Phe Glu Pro Glu Asp Thr Gly Gln Arg Val Pro Val Ser
            80                  85                  90

CAC AGC TTC CCA CAC CCG CTC TAC AAT ATG AGC CTT CTG AAG CAT CAA      336
His Ser Phe Pro His Pro Leu Tyr Asn Met Ser Leu Leu Lys His Gln
        95                  100                 105

AGC CTT AGA CCA GAT GAA GAC TCC AGC CAT GAC CTC ATG CTG CTC CGC      384
Ser Leu Arg Pro Asp Glu Asp Ser Ser His Asp Leu Met Leu Leu Arg
110                 115                 120                 125

CTG TCA GAG CCT GCC AAG ATC ACA GAT GTT GTG AAG GTC CTG GGC CTG      432
Leu Ser Glu Pro Ala Lys Ile Thr Asp Val Val Lys Val Leu Gly Leu
                130                 135                 140

CCC ACC CAG GAG CCA GCA CTG GGG ACC ACC TGC TAC GCC TCA GGC TGG      480
Pro Thr Gln Glu Pro Ala Leu Gly Thr Thr Cys Tyr Ala Ser Gly Trp
                145                 150                 155

GGC AGC ATC GAA CCA GAG GAG TTC TTG CGC CCC AGG AGT CTT CAG TGT      528
```

```
Gly Ser Ile Glu Pro Glu Glu Phe Leu Arg Pro Arg Ser Leu Gln Cys
            160                 165                 170

GTG AGC CTC CAT CTC CTG TCC AAT GAC ATG TGT GCT AGA GCT TAC TCT      576
Val Ser Leu His Leu Leu Ser Asn Asp Met Cys Ala Arg Ala Tyr Ser
    175                 180                 185

GAG AAG GTG ACA GAG TTC ATG TTG TGT GCT GGG CTC TGG ACA GGT GGT      624
Glu Lys Val Thr Glu Phe Met Leu Cys Ala Gly Leu Trp Thr Gly Gly
190                 195                 200                 205

AAA GAC ACT TGT GGG GGT GAT TCT GGG GGT CCA CTT GTC TGT AAT GGT      672
Lys Asp Thr Cys Gly Gly Asp Ser Gly Gly Pro Leu Val Cys Asn Gly
                210                 215                 220

GTG CTT CAA GGT ATC ACA TCA TGG GGC CCT GAG CCA TGT GCC CTG CCT      720
Val Leu Gln Gly Ile Thr Ser Trp Gly Pro Glu Pro Cys Ala Leu Pro
            225                 230                 235

GAA AAG CCT GTT GTG TAC ACC AAG GTG GTG CAT TAC CGG AAG TGG ATC      768
Glu Lys Pro Val Val Tyr Thr Lys Val Val His Tyr Arg Lys Trp Ile
        240                 245                 250

AAG GAC ACC ATC GCA GCC AAC CCC TGAGTGCCCC TGTCCCACCC CTACCTCTAG     822
Lys Asp Thr Ile Ala Ala Asn Pro
255                 260

TAAACTGCAG                                                           832

(2) INFORMATION FOR SEQ ID NO:21:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Ile Val Gly Gly Trp Glu Cys Glu Lys His Ser Gln Pro Trp Gln Val
1               5                   10                  15

Ala Val Tyr Ser His Gly Trp Ala His Cys Gly Gly Val Leu Val His
                20                  25                  30

Pro Gln Trp Val Leu Thr Ala Ala His Cys Leu Lys Lys Asn Ser Gln
            35                  40                  45

Val Trp Leu Gly Arg His Asn Leu Phe Glu Pro Glu Asp Thr Gly Gln
    50                  55                  60

Arg Val Pro Val Ser His Ser Phe Pro His Pro Leu Tyr Asn Met Ser
65                  70                  75                  80

Leu Leu Lys His Gln Ser Leu Arg Pro Asp Glu Asp Ser Ser His Asp
                85                  90                  95

Leu Met Leu Leu Arg Leu Ser Glu Pro Ala Lys Ile Thr Asp Val Val
            100                 105                 110

Lys Val Leu Gly Leu Pro Thr Gln Glu Pro Ala Leu Gly Thr Thr Cys
    115                 120                 125

Tyr Ala Ser Gly Trp Gly Ser Ile Glu Pro Glu Glu Phe Leu Arg Pro
130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
            180                 185                 190

Leu Val Cys Asn Gly Val Leu Gln Gly Ile Thr Ser Trp Gly Pro Glu
    195                 200                 205
```

-continued

```
Pro Cys Ala Leu Pro Glu Lys Pro Val Val Tyr Thr Lys Val Val His
    210                 215                 220
Tyr Arg Lys Trp Ile Lys Asp Thr Ile Ala Ala Asn Pro
225                 230                 235
```